(12) United States Patent
Stetter et al.

(10) Patent No.: US 9,784,708 B2
(45) Date of Patent: Oct. 10, 2017

(54) PRINTED GAS SENSOR

(71) Applicant: KWJ Engineering Inc., Newark, CA (US)

(72) Inventors: Joseph R. Stetter, Hayward, CA (US); Vinay Patel, Fremont, CA (US); Melvin W. Findlay, Buchanan, GA (US); Michael T. Carter, Denver, CO (US)

(73) Assignee: SPEC SENSORS, LLC, Newark, CA (US)

( * ) Notice: Subject to any disclaimer, the term of this patent is extended or adjusted under 35 U.S.C. 154(b) by 503 days.

(21) Appl. No.: 14/317,222

(22) Filed: Jun. 27, 2014

(65) Prior Publication Data

US 2014/0311905 A1 Oct. 23, 2014

Related U.S. Application Data

(60) Continuation-in-part of application No. 13/740,327, filed on Jan. 14, 2013, now Pat. No. 8,795,484, which
(Continued)

(51) Int. Cl.
*G01N 27/404* (2006.01)
*B01J 31/06* (2006.01)
(Continued)

(52) U.S. Cl.
CPC .......... *G01N 27/4045* (2013.01); *B01J 31/06* (2013.01); *C09D 11/03* (2013.01);
(Continued)

(58) Field of Classification Search
CPC ............ G01N 27/404; G01N 27/4045; C09D 11/106; C09D 11/03; B32B 38/145; B32B 38/0004; B32B 2323/10; B32B 2310/0806; B32B 2310/0843; B32B 2309/105; B32B 2457/00; Y10T 156/10
See application file for complete search history.

(56) References Cited

U.S. PATENT DOCUMENTS 4,924,860 A 5/1990 Larsen et al.
4,945,918 A 8/1990 Abernathy
(Continued)

FOREIGN PATENT DOCUMENTS

CA 2270809 10/1999
DE 2936142 3/1981
(Continued)

OTHER PUBLICATIONS

Korotcenkov et al, "Review of Electrochemical Hydrogen Sensors," Chemical Reviews 109(3):1402-1433 (2009).
(Continued)

*Primary Examiner* — J. Christopher Ball
(74) *Attorney, Agent, or Firm* — Dinsmore & Shohl LLP

(57) ABSTRACT

A printed gas sensor is disclosed. The sensor may include a partially porous substrate, an electrode layer, an electrolyte layer, and an encapsulation layer. The electrode layer comprises one or more electrodes that are formed on one side of the porous substrate. The electrolyte layer is in electrolytic contact with the one or more electrodes. The encapsulation layer encapsulates the electrode layer and electrolyte layer thereby forming an integrated structure with the partially porous substrate.

56 Claims, 11 Drawing Sheets

Related U.S. Application Data is a division of application No. 12/953,672, filed on Nov. 24, 2010, now abandoned.

(51) Int. Cl.
| | | |
|---|---|---|
| *C09D 11/03* | (2014.01) | |
| *C09D 11/106* | (2014.01) | |
| *C09D 11/52* | (2014.01) | |
| *B32B 37/18* | (2006.01) | |
| *B32B 38/00* | (2006.01) | |

(52) U.S. Cl.
CPC ............ *C09D 11/106* (2013.01); *C09D 11/52* (2013.01); *B32B 37/185* (2013.01); *B32B 38/0004* (2013.01); *B32B 38/145* (2013.01); *B32B 2309/105* (2013.01); *B32B 2310/0806* (2013.01); *B32B 2310/0843* (2013.01); *B32B 2323/10* (2013.01); *B32B 2457/00* (2013.01)

(56) References Cited

U.S. PATENT DOCUMENTS

| | | | |
|---|---|---|---|
| 5,064,516 | A | 11/1991 | Rupich |
| 5,173,166 | A | 12/1992 | Tomantschger et al. |
| 5,233,996 | A | 8/1993 | Coleman et al. |
| 5,239,492 | A | 8/1993 | Hartwig |
| 5,288,389 | A | 2/1994 | Yamada et al. |
| 5,429,105 | A | 7/1995 | Bennett et al. |
| 5,438,876 | A | 8/1995 | Lewis |
| 5,595,646 | A | 1/1997 | Foos et al. |
| 5,670,949 | A | 9/1997 | Kirby et al. |
| 5,876,577 | A | 3/1999 | McAleer et al. |
| 5,945,069 | A | 8/1999 | Buehler |
| 6,099,708 | A | 8/2000 | Mallory et al. |
| 6,158,431 | A | 12/2000 | Poole |
| 6,234,006 | B1 | 5/2001 | Sunshine et al. |
| 6,254,749 | B1 | 7/2001 | Yokota et al. |
| 6,454,923 | B1 | 9/2002 | Dodgson et al. |
| 6,513,362 | B1 | 2/2003 | Yadav et al. |
| 6,590,207 | B2 | 7/2003 | Berger et al. |
| 6,645,361 | B1 | 11/2003 | Bloemer et al. |
| 6,713,389 | B2 | 3/2004 | Speakman |
| 6,936,147 | B2 | 8/2005 | Prohaska et al. |
| 6,940,287 | B2 | 9/2005 | Weyl et al. |
| 7,077,938 | B1 | 7/2006 | Austen et al. |
| 7,189,341 | B2 | 3/2007 | Li et al. |
| 7,279,080 | B2 | 10/2007 | Chapples et al. |
| 7,422,646 | B2 | 9/2008 | Prohaska et al. |
| 7,445,941 | B2 | 11/2008 | Buechler |
| 8,152,991 | B2 | 4/2012 | Briman et al. |
| 8,747,635 | B2 | 6/2014 | Murakami et al. |
| 2002/0166769 | A1 | 11/2002 | Serikov |
| 2003/0208133 | A1 | 11/2003 | Mault |
| 2004/0135684 | A1 | 7/2004 | Steinthal et al. |
| 2004/0213702 | A1 | 10/2004 | Ingrisch |
| 2005/0274615 | A1 | 12/2005 | Naito et al. |
| 2006/0096871 | A1 | 5/2006 | Manoukian et al. |
| 2006/0191318 | A1 | 8/2006 | McBride et al. |
| 2007/0102294 | A1 | 5/2007 | Dorisio Deininger et al. |
| 2007/0144812 | A1 | 6/2007 | Stewart et al. |
| 2007/0154748 | A1 | 7/2007 | Okuyama et al. |
| 2008/0190174 | A1 | 8/2008 | Kooi et al. |
| 2008/0202930 | A1 | 8/2008 | Mett |
| 2008/0289962 | A1 | 11/2008 | Prohaska et al. |
| 2009/0040044 | A1 | 2/2009 | Chiao |
| 2009/0162750 | A1 | 6/2009 | Kawakami et al. |
| 2010/0057401 | A1 | 3/2010 | Scheffler et al. |
| 2010/0226824 | A1 | 9/2010 | Ophir et al. |
| 2011/0226041 | A1 | 9/2011 | Cummins |
| 2011/0246090 | A1 | 10/2011 | Goya |
| 2011/0288430 | A1 | 11/2011 | Varney et al. |
| 2012/0006096 | A1 | 1/2012 | Ackley et al. |
| 2012/0125772 | A1 | 5/2012 | Stetter et al. |
| 2012/0140431 | A1 | 6/2012 | Faxvog et al. |
| 2013/0265140 | A1 | 10/2013 | Gudan et al. |
| 2014/0018691 | A1 | 1/2014 | McNeill |
| 2014/0029085 | A1 | 1/2014 | Bond et al. |
| 2014/0174154 | A1 | 6/2014 | Marra et al. |
| 2014/0208829 | A1 | 7/2014 | Lechner et al. |
| 2014/0257127 | A1 | 9/2014 | Smith et al. |
| 2014/0311905 | A1 | 10/2014 | Stetter et al. |

FOREIGN PATENT DOCUMENTS

| | | |
|---|---|---|
| DE | 3809107 | 9/1989 |
| DE | 19832395 | 11/1999 |
| GB | 2440556 | 2/2008 |
| JP | 05-099886 | 4/1993 |
| JP | 08-327591 | 12/1996 |
| WO | 9012315 | 10/1990 |
| WO | WO96/14576 | 5/1996 |
| WO | WO98/25138 | 6/1998 |
| WO | WO01/14864 | 3/2001 |
| WO | 2005114162 | 12/2005 |
| WO | 2013123500 | 8/2013 |
| WO | 2014143049 | 9/2014 |

OTHER PUBLICATIONS

International Search Report and Written Opinion issued in corresponding PCT International Application No. PCT/US0211/059075, dated Jan. 24, 2012.

International Search Report and Written Opinion mailed on Oct. 2, 2015 in International Patent Application No. PCT/US2015/037893.

Wang, J., "Decentralized Electrochemical Monitoring of Trace Metals: From Disposable Strips to Remote Electrodes," Analyst 119:763-766 (1994).

Stetter, J.R., "Instrumentation to Monitor Chemical Exposure in the Synfuel Industry," Annals American Conf. of Governmental and Industrial Hygienists, 11:225-269 (1984).

Korotcenkov et al, "Review of Electrochemical Hydrogen Sensors," Chemical Reviews 109(3)1402-1433 (2009).

Stetter, J.R. et al, "Amperometric Gas Sensors-A Review," Modern Topics in Chemical Sensing: Chapter 4, Chemical Reviews, 108 (2):352-366 (2008).

Chang, S.C., et al, "Amperometric Gas Sensors", Talanta, 40(4):461-467 (1993).

International Search Report and Written Opinion issued in corresponding PCT International Application No. PCT/US2011/059075, dated Jan. 24, 2012.

International Search Report and Written Opinion issued in corresponding PCT International Application No. PCT/US2015/037893, dated Oct. 2, 2015.

International Search Report and Written Opinion issued in corresponding PCT International Application No. PCT/US2015/049631, dated Dec. 14, 2015.

International Search Report and Written Opinion issued in corresponding PCT International Application No. PCT/US2015/068251, dated Mar. 11, 2016.

International Search Report and Written Opinion issued in corresponding PCT International Application No. PCT/US2016/034314, dated Sep. 2, 2016.

International Search Report and Written Opinion issued in corresponding PCT International Application No. PCT/US2015/046053, dated Oct. 28, 2015.

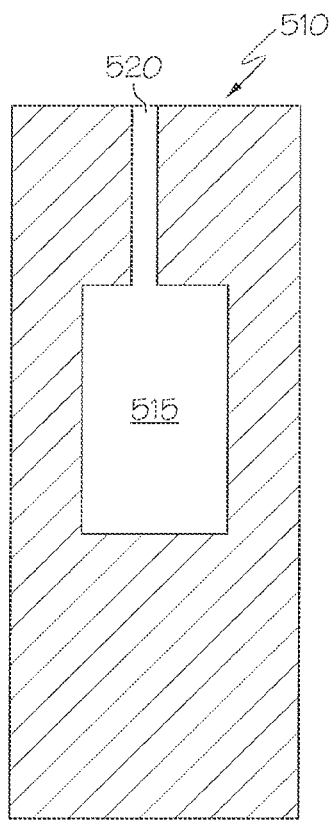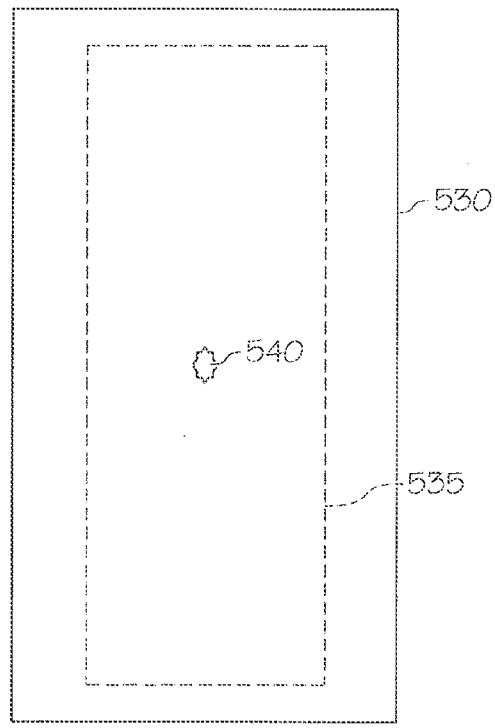
FIG. 3A    FIG. 3B
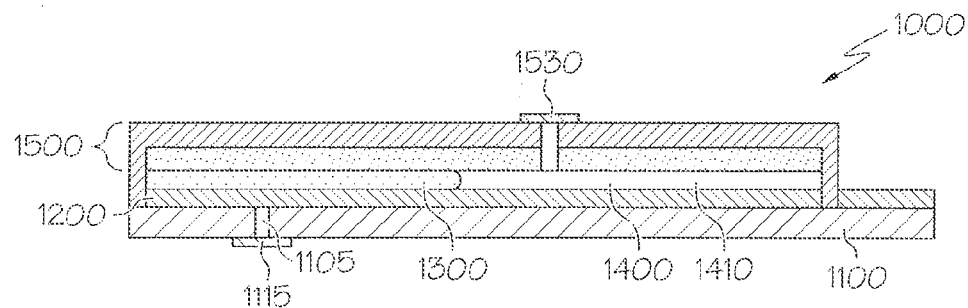
FIG. 4

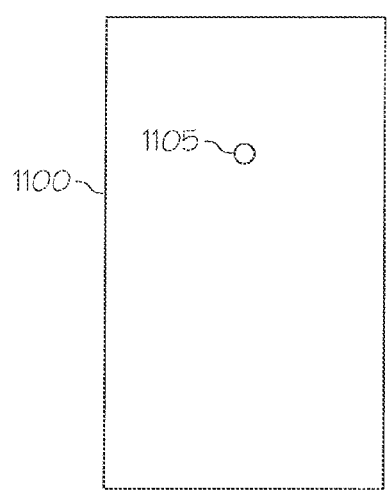
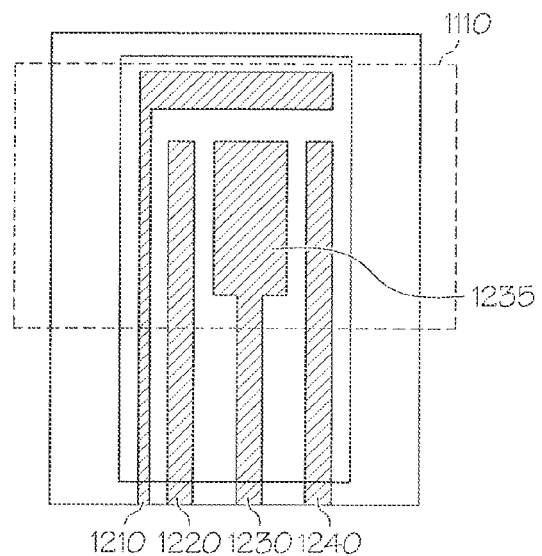
FIG. 5  FIG. 6
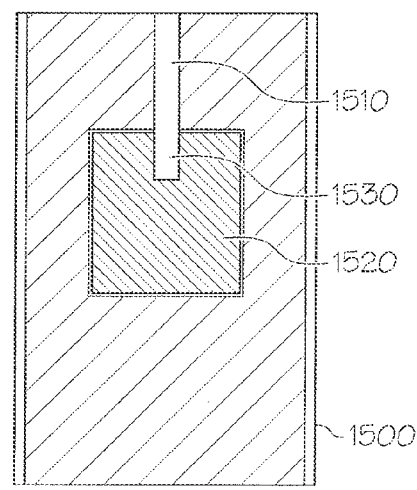
FIG. 7

PRINTED GAS SENSOR

RELATED APPLICATIONS

This application is a continuation-in-part of U.S. patent application Ser. No. 13/740,327 filed Jan. 14, 2013 which is a divisional of U.S. patent application Ser. No. 12/953,672 filed Nov. 24, 2010, the entire disclosures of which are hereby incorporated by reference.

TECHNICAL FIELD

The following disclosure relates generally to printed gas sensors, and in particular to a printed gas sensor comprising a liquid, polymer, solid, or gel electrolyte and a method thereof.

BACKGROUND

Electrochemical cells have been used for detection of toxic gases since the 1970s in, for example, fixed location instrumentation for infrastructure (such as buildings and parking garages) and portable safety and inspection equipment used in transportation. For example, see Stetter, J. R., "Instrumentation to Monitor Chemical Exposure in the Synfuel Industry," Annals American Conf. of Governmental and Industrial Hygienists, 11, 225-269, (1984). These sensors may be preferred in ambient monitoring applications because of their accuracy at low detection levels, selectivity, linearity, and power requirements. Industrial-grade electrochemical cells can cost the customer over $25 each and even several hundred dollars without any electronics, even when manufactured in high volumes. This cost can significantly increase the cost of gas monitors and detectors, and can leave manufacturers with few cost-effective options to create ultra-cheap, yet high performance gas detectors. For example, high quality, accurate devices for sensing carbon monoxide and triggering an alarm in the presence of excessive concentrations of carbon monoxide (CO) that may be hazardous to life or health are presently available for many industrial applications, but such devices are still too costly for use in most homes.

As a result, less expensive sensors with much lower performance are chosen to meet high volume consumer product cost goals, resulting in lower performance and a sacrifice of needed safety and health protection for the consumer. Additional consumer, medical, and industrial applications will be made available with a significant reduction in the cost and dimensions of electrochemical gas sensors. Other prior art gas sensors may use a liquid proton conductor where the outside surfaces of the sensing and counter electrodes of the sensor are coated by NAFION™ layers. NAFION™ is subject to freezing at 0° C., hindering operation of a sensor coated by NAFION™ at temperature of 0° C. and below. Further, the lifetime of these sensors can range from about 6-12 months due to rapid drying of the liquid electrolyte. Thus, the sensor requires maintenance due to liquid electrolyte evaporation, leakage, and/or corrosion. In addition, the sensors can have significant manufacturing costs and be relatively large, sometimes with large electrolyte or water reservoirs, which make integration of these sensors into modern equipment or small personal monitors difficult.

Another prior art gas sensor uses a design incorporating proton conductors, one type of electronically conductive metal catalyst for the sensing electrode, and a different type of electronically conductive metal catalyst for the counter electrode. This allows the sensing electrode to decompose a gas to produce protons and electrons, while the counter electrode exhibited no activity to decompose the gas. The result is a Nernst potential between the two electrodes, which can be used to detect a target gas. However, issues that could result from such a design include the gas reaction being carried out slowly or interfering reactions occurring on one or the other electrode surface. Additionally, the response signal could be weak. Further, the Nernst potential may be difficult to zero in clean air and the calibration is limited to about 59 mV per decade of concentration. Again poor electrolyte or electrode stability over time can degrade performance of a potentiometric gas sensor which often operate better at a high temperature.

Thus, a competitive electrochemical sensor that can cost less to manufacture in high volume and has high performance and small size, that would create a new opportunity for companies to develop low-cost gas detectors that could be manufactured in high volumes, thus making high accuracy detectors, for example, those that monitor and detect carbon monoxide and protect people and assets, much less expensive. This cost reduction, without loss in performance, could revolutionize and tremendously expand the use of gas detectors in their application, including home carbon monoxide monitors, automobile air quality, and building ventilation and controls. In addition, new applications would become possible, including safety organizations that may desire to inexpensively protect or monitor a large area from toxic gases like carbon monoxide, and universities or scientific/environmental organizations wanting to study toxic gas levels over large areas. In addition, an electrochemical sensor that also can be small can be used in cell-phones to enable worldwide networks of CO and other gas monitors.

The traditional porous, composite electrode is comprised of 10-40% polytetrafluoroethylene (PTFE) by weight and 60-90% catalyst by weight. The traditional electrode has possible residual dispersing, surfactants and thickening agents. These residual components are chemically inert and electrochemically inert. These electrodes are cured and/or sintered near the melting point of PTFE, typically 290-310 C. This requires printing on substrates such as porous PTFE that can withstand the PTFE cure temperatures. The PTFE serves as a binder to hold the catalyst particles together in a porous bed. It also serves as the hydrophobic portion of the composite bed electrode to provide a proper environment for a triple-phase boundary. This triple-phase boundary is desirous for gas-phase amperometric sensors.

While a variety of devices and techniques may exist for detecting gases, it is believed that no one prior to the inventors has made or used the inventive embodiments as described herein which have allowed the thin and tiny form factors and the low cost assembly achieved herein together with the high performance.

SUMMARY

In one example, a printed gas sensor is disclosed. The sensor may comprise: a substrate that is at least partially gas porous or gas permeable; an electrode layer, wherein the electrode layer comprises two or more electrodes, with one at least partially porous electrode, that are formed on one side of said porous substrate; a solid, liquid, gel or similarly functional electrolyte layer, wherein the electrolyte layer is in electrolytic contact with the electrode layer, and an encapsulation layer, wherein the encapsulation layer encapsulates the electrode layer and part or all of its substrate and electrolyte layer, thereby forming an integrated structure with the porous substrate.

In another example, a printed gas sensor is disclosed that may comprise: a porous substrate; an electrode layer, wherein the electrode layer comprises two or more porous electrodes that are formed on one side of said porous substrate; a wicking layer formed on the electrode layer; a solid, liquid, or gel electrolyte layer, wherein the electrolyte layer is in electrolytic contact with the two or more electrodes; and an encapsulation layer, wherein the encapsulation layer encapsulates the electrode layer, wicking layer and electrolyte layer thereby forming an integrated structure with the porous substrate.

In still another example, a method for manufacturing a printed gas sensor is disclosed. The method comprises printing two or more electrodes with one at least partially porous electrode onto one side of the at least partially porous substrate using a metal catalyst ink; curing the porous substrate; bonding an optional encapsulation layer having a capillary channel to the porous substrate thereby encapsulating the two or more porous electrodes and forming an electrolyte reservoir; filling the electrolyte reservoir through the capillary channel with a liquid or gel electrolyte; and sealing the capillary channel.

In a further example, porous gas electrodes comprise alternative polymer components replacing the standard PTFE aqueous dispersion particles. In some examples, the standard PTFE particles are replaced with dry PTFE particles. In other examples, the standard PTFE particles are replaced with polypropylene or polyethylene particles.

While the specification concludes with claims, which particularly point out and distinctly claim the invention, it is believed the present invention will be better understood from the following description of certain examples taken in conjunction with the accompanying drawings. In the drawings, like numerals represent like elements throughout the several views.

BRIEF DESCRIPTION OF THE DRAWINGS

FIGS. 3A & 3B depict an encapsulation layer of the exemplary printed sensor shown in FIG. 1.

FIG. 4 depicts an exemplary version of a printed sensor in cross section view.

FIG. 5 depicts a substrate layer of the exemplary printed sensor shown in FIG. 4.

FIG. 6 depicts a substrate and electrode layer of the exemplary printed sensor shown in FIG. 4.

FIG. 7 depicts an encapsulation layer of the exemplary printed sensor shown in FIG. 4.

Figure 1:
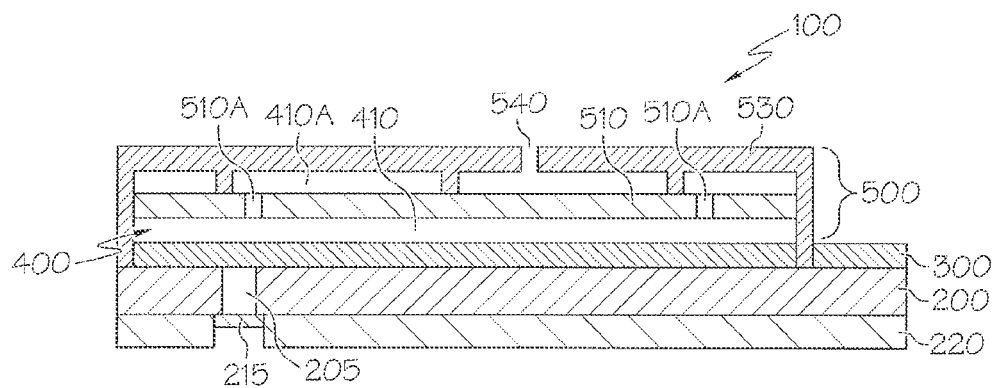
FIG. 1 depicts an exemplary version of a printed sensor in cross section view.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

Examples described herein include a printed gas sensor comprising: a porous substrate; an electrode layer, wherein the electrode layer comprises two or more electrodes that are formed on one side of said porous substrate; a liquid or gel electrolyte layer, wherein the electrolyte layer is in electrolytic contact with the two or more electrodes; and an encapsulation layer, wherein the encapsulation layer encapsulates the electrode layer and electrolyte layer thereby forming an integrated structure with the porous substrate. The printed gas sensor may be used to detect and measure a wide range of target gaseous components. By way of example only, it can be used to detect CO, $H_2S$, NO, $NO_2$, $SO_2$, $O_3$, and related compounds that can be either electro-oxidized or electro-reduced compounds. For exemplary electro-oxidized and electro-reduced compounds see: Stetter, J. R. Sang-Do, Han, and G. Korotchenkov, "Review of Electrochemical Hydrogen Sensors," Chemical Reviews 109(3), 2009, pp 1402-1433; Joseph R. Stetter and Jing Li, in Modern Topics in Chemical Sensing: Chapter 4, "Amperometric Gas Sensors—A Review," Chemical Reviews, 108 (2), 2008, pp 352-366; Chang, S. C., Stetter, J. R., Cha, C. S., "Amperometric Gas Sensors", Talanta, 40, No. 4, pp 461-467, (1993).

The porous substrate is gas permeable at least in part and has porosity sufficient to allow a gas sample to permeate through and react at the working electrode which is also sufficiently porous to allow the sample to diffuse to the metal surface and react. In one exemplary embodiment, when an aqueous or hydrophilic room temperature ionic liquid (RTIL) electrolyte is utilized, the porous membrane is selected from hydrophobic membranes. In an alternative embodiment, when a hydrophobic organic electrolyte (i.e. an ionic liquid or more particularly an RTIL, a salt in the liquid state that primarily comprises ions and short-lived ion pairs) is utilized, the porous membrane is selected from oligophobic membranes. This can be measured by the contact angle. In some preferred embodiments, the contact angle of the RTIL/organic electrolytes on the chosen membrane is the same or greater than the contact angle for water or sulfuric acid (about 90°) on the chosen membrane. Exemplary membranes can be hydrophobic or hydrophillic. Exemplary porous hydrophobic and oligophobic membranes include PTFE (e.g., MuPor™ by Porex™ and Zitex™ by Saint-Gobain™), polypropylene (e.g. polypropylene filters by Pall™, polypropylene membranes by Sterlitech™), polycarbonate (e.g., polycarbonate track etch (PCTE) membrane disc filters by Sterlitech™), and PVDF (e.g., Immobilon™ by Millipore™). Exemplary porous hydrophillic membranes include polyethersulfone (e.g., polyethersulfone membranes by Pall™), surface modified PVC (e.g., PVC with ozone induced graft polymerization), and surface modified polypropylene (e.g., polypropylene with UV radiation). Exemplary membranes can also be made by treating a porous membrane with cytop to make the porous membrane hydrophobic, derivatizing a surface of a porous membrane with silane to make the surface hydrophobic, or selecting surface treatment chemistry with a desired level of hydrophobicity or oligophobicity.

Embodiments of a printed gas sensor described herein can utilize electrolytes, such as RTILs or $H_2SO_4$ having certain contact angles. Ranges of working contact angles allow a generalization as to which type of RTILs or other electrolytes can be chosen based on the range of contact angles. These contact angles are important for viable gas sensor performance of the membrane of the printed gas sensor. The contact angles of exemplary RTIL electrolytes listed below are contact angle measurements of a 2 µL droplet of each exemplary electrolyte on MuPor porous PTFE. 4M $H_2SO_4$ has about a 118° contact angle, 1-Hexyl-3-methylimidazolium bis(trifluoromethylsulfonyl)imide has about a 99° contact angle, 1-Ethyl-3-methylimidazolium bis(trifluoromethylsulfonyl)imide has about a 106° contact angle, 1-Butyl-3-methylimidazolium bis(trifluoromethylsulfonyl)imide has about a 90° contact angle, 1-ethyl-3-methylimidazolium ethyl sulfate has about a 113° contact angle, 1-butyl-3-methylimidazolium tetrafluoroborate has about a 139° contact angle, 1-ethyl-3-methylimidazolium tetrafluoroborate has about a 122° contact angle, 1-butyl-1-methylpyrrolidinium dicyanamide has a contact angle between about 131° and 134°, and 1-butyl-1-methylpyrrolidinium bis[(trifluoromethyl)sulfonyl]imide has about a 71° contact angle. In some embodiments of the printed gas sensor, it is desirous to have an electrolyte comprising an RTIL having a contact angle greater than 115°. This provides a high quality response in measurements of hydrogen sulfide and ozone and should be suited to other gas measurement chemistries.

In one exemplary embodiment, the substrate is porous PTFE [e.g. trade names Zitex™ Gortex™, or MuPor™] and the electrode metal material is applied as an ink composite to make a porous gas diffusion electrode. Further, the porous or partially porous substrate may comprise porous polymeric materials, such as porous polytetrafluoroethylene, porous polyethylene, porous polypropylene, porous polyisobutylene, porous polyester, porous polyurethane, porous polyacrylic, porous fluorine polymer, porous cellulosic polymer, porous fiberglass that may be treated to alter the hydrophobicity or oligophobicity, any other porous non-reactive thermoplastic, or composites or mixtures thereof. In some embodiments, the porous or partially porous substrate is non-wettable. The porous substrate thickness can range typically from about 100 microns to 250 microns and may include pores having diameters in the range of about 0.1 micron to about 5 microns. The porous substrate can be any thickness and can have any pore diameter that creates the appropriate porosity. The porous substrate can be placed on a backplate 220 or support with a controlled-size hole [see FIG. 5] that allows the appropriate gas access into the sensor's working electrode. The thickness of this backplate or support/porous substrate can be 0.002 to 0.005 inches and can comprise polyethylene terephthalate (PET), polycarbonate, polypropylene or other suitable plastic as shown in FIGS. 4 and 5 but any thickness to create the selected or desired gas access is acceptable. The two layers can be laminated, glued or otherwise placed and held adjacent to one another. In another embodiment, the backplate access hole provides the porous entry and obviates the need for a separate and distinct porous or partially porous substrate.

The porous substrate can have an access port for entry of a gas sample to be measured. The access port should be sized to allow a gas sample to enter the sensor, but not too large such that supply of the gas sample is beyond the capacity of the electrodes or the desired range of reactivity. For example, the access port hole may range in size from about 0.003 inches in diameter to about 0.080 inches in diameter. The larger hole can be desired for lower concentrations (e.g. a 1-10 ppm CO sensor) while the smaller hole can be chosen for a broader range sensor (e.g. a 0-10,000 ppm CO sensor). The access port may also be larger or smaller and depend upon the gas to be detected, the range of the sensor desired, and the particular construction and need of the sensing reaction and sensor mechanism of response (e.g., diffusion limited signal, or reaction rate limited signal, or other limitation of the overall electrochemical sensor). The access port may be formed by stamping, laser cutting, die cutting, drilling, or other known exemplary processes. The access port may be a single porous area or hole or a collection of pores or holes or materials that have gas permeability to allow the analyte to enter. The access port may contain a reactive material to selectively allow the analyte to pass and retain certain unwanted interferences. In operation, a gas sample may enter through the access port and pass through the, sometimes optional, porous substrate on the side opposite of the electrode layer in order to reach the working electrode and react. Further, the gas sample may permeate through the access port. The access port can be a straight through hole as shown in the figures or a tortuous path with or without obstructions or filter materials. This allows gas access of the analyte to the working electrode electrolyte interface.

The access port may be covered by a filter, which is adhered to or otherwise held in place next to the access port of the substrate. By way of example only, the filter can comprise any material that protects the electrode layer from poisoning or clogging particles or any other unwanted direct exposure to the environment from which the target analyte (that which is to be analyzed) originates. By way of example only, the filter can also comprise any material that can remove the effects of wind and dust, evaporation of the electrolyte from the sensor and reduce effects of pressure fluctuations and air turbulence on the gas sensor. By way of example only, the filter can also comprise any material that may remove interferents, for example, hydrogen sulfide in a CO gas sensor, so that a target gas, CO in this example, may pass through to the electrode layer unimpeded. Examples of a filter can include porous polytetrafluoroethylene (PTFE), carbon, impregnated carbon cloth, $KMnO_4$ on alumina, and reactive material in the form of powder or composite and a tortuous path. Filters for NO can include triethanolamine on a silica support. As one skilled in the art will appreciate, there are other chemistries that can be developed for gas sensing for selective filters based on acid-base and other absorptive or reactive and other chemistries. For example, Cu-Acetate, bicarbonate, or similar basic salts can be used to remove acid gases like H2S or SO2. For ammonia removal, an acid media such as an acid washed alumina substrate can be used; however, this can remove basic gases. The media should be dispersed in order to remove the gases efficiently without impeding the gas sample flow to the sensor.

The electrode layer comprises two or more electrodes that may be designed to provide a high or low surface area to control the electrode-electrolyte interface and maximize the current output of the sensor and minimize the noise in the sensor. The optimum analytical signal for the target analyte will be a combination of considerations of signal, background, noise, and interferences. The electrode layer can act as a gas-permeable membrane and provide a physical boundary between the electrolyte and the gas. This physical structure of the working electrode is important to control and this control is offered by control of the ink formulation and curing process. The electrode material can also be sputtered or physically or chemically deposited onto or made to lie next to the substrate layer. The electrode layer may be formed on one side of the porous substrate by screen printing or inkjet printing. The thickness of the electrode layer may range from about 100 nanometers to about 125 microns (0.005 inches or 5 mil) typically but of course can be any thickness that is effective at reacting the analyte. Screen printing typically produces layers that are 0.001-0.005 inches depending on the ink formulation and the screen mesh size used to deposit the composite material. In one exemplary embodiment, screen printing is attractive because it is a fast, efficient process and can print multiple electrodes at the same time (i.e. the two or more electrodes needed for sensor operation) and multiple devices on a large substrate area, simultaneously. The materials for the screen printing can be any range of materials needed for the electrode including Pt particles for CO sensors and Au particles for $H_2S$ sensors and SWCNT (single walled carbon nanotubes) for Ozone sensors.

The electrode layer only requires two electrodes but more than two are possible. A first electrode may be referred to as the sensing or working electrode and comes into contact with a target gas sample that is to be detected. A second electrode may be known as the counter, auxiliary, counter-reference, or common electrode. When the target gas to be detected comes in contact with the sensing electrode, an oxidation or reduction reaction takes place at the sensing electrode, with a corresponding reduction or oxidation reaction occurring at the counter electrode.

For example, in the case of a carbon monoxide gas sensor, the following oxidation/reduction reaction may occur. Carbon monoxide is oxidized as follows:

$$CO + H_2O \rightarrow CO_2 + 2H^+ + 2e^- \quad (1)$$

In the corresponding reduction reaction, the protons (hydrogen ions) migrate across a proton conductive electrolyte membrane to a counter electrode where they may react with oxygen as follows:

$$2H^+ + 2e^- + \tfrac{1}{2}O_2 \rightarrow H_2O \quad (2)$$

It may be desirous to include an additional or third electrode with a constant or almost constant potential throughout the reaction. Such an electrode may be called the reference electrode and can play a role in stabilizing the potential of the sensing electrode. Alternatively, the counter electrode may be non-polarizable and act as a reference electrode. The sensor is interfaced with suitable electronic components to read out the current as a measure of the reacting gas concentration. Further, if the currents in the sensor are small enough with respect to the size of the sensor electrodes to minimally polarize the counter electrode, then the counter electrode can be used as a reference electrode in a three electrode circuit. These suitable electronic components can non-exhaustively include circuits such as current to voltage convertors, potentiostats, amperostats, and current mirrors. A galvanic sensor operation and circuit is also possible in some cases.

The electrode layer may typically comprise from about 60% to about 90% of a metal catalyst, from about 2% to about 40% of polymer (e.g., micron-sized Teflon particles), in an ink formulation that contains less than about 10% of an optional binder, less than about 10% of an optional surfactant and from about 0% to about 10% of one or more optional modifiers. The binder is designed to remain in the electrode and provide structural support while the modifier can be an additive that alters properties of the electrode such as wetting character or porosity. The metal catalyst may be a powder and, by way of example only, may comprise Pt, Pd, Au, Ag, Ru, Rh, Ir, Co, Fe, Ni, C, or other noble or reactive metals, and alloys or admixtures thereof. The metal catalyst may be a carbon supported catalyst. For example, the carbon support may be nanoparticulate carbon, ball-milled graphitic carbon, single walled carbon nanotubes, Au nanoparticles, or any suitable support. The binder can assist in providing the ink formulation with a proper viscosity and vaporization/drying rate for screen printing and/or function to hold the ink to the substrate and merge with the substrate during the curing process to control electrode properties such as hydrophobicity, hydrophilicity and/or porosity (amount and type). Examples of suitable binders include Nicrobraz-S (available from Wall Colmonoy Corporation located in Madison Heights, Mich.), or solutions of polyvinyl alcohol (PVA). Other suitable binders include silicate or aluminate materials, or polymers such as ethyl cellulose. The surfactant can act as the solution stabilizer for the ink composite and may comprise solvents, such as water, triton-100, carbopol or other material. The modifiers comprise small amounts of additives, which can be active in controlling the behavior of the inks before, during, and/or after processing and curing. Suitable modifiers may include polyvinyl alcohol, 1-propanol, gum arabic, sodium n-dodecyl sulfate, ethanol, or a composite material. The materials used in the ink composition should generally evaporate or bake out of the composite electrode during a curing process, or the materials should be electrochemically inert and not alter electrode performance, porosity, or wettability in an intended way. The materials used in ink composition should generally leave behind an electrode catalyst of the desired porosity, chemistry, density, and hydrophobicity or hydrophilicity for optimum interaction with the electrolyte and analyte gas. Other suitable components for this ink formulation will be apparent to those of ordinary skill in the art in view of the teachings herein on controlling the proper chemical and physical properties of electrodes for gas sensing.

The electrode layer is in electrolytic contact with the electrolyte layer. The electrolyte layer can be any suitable material capable of providing the needed electrolytic system for the sensing and counter reactions and interface to the electrodes. Suitable electrolytes include aqueous systems of acids, bases, and salts as well as polymer electrolytes like Nafion, or non-aqueous systems like propylene carbonate lithium perchlorate, polyethylene oxide lithium chloride, or ionic liquids. The electrode layer may also be in electrical communication with a measurement device, such as a potentiostat circuit. Electrical communication may comprise the electrode layer having tracks screen printed directly on the substrate, such as printed runners and conductive traces, which connect the two or more electrodes to a potentiostat circuit. The electrode layer may be connected to the potentiostat circuit exterior to the gas sensor through the tracks. Electrical communication may also comprise wire connections running from the electrodes through the gas sensor to the potentiostat circuit.

In some embodiments, the electrode connections run from the active area of sensing at the working electrode inside the sensor to outside the sensor through a path that is sealed to any material flow. Such a configuration minimizes and/or eliminates electrolytes, ions, gases, liquids, or solids of any kind transporting across the seal. The printed runner is comprised of a conductor through which electrons can flow but materials cannot flow, such as, for example, a conductive trace having conductive ink. A printed runner's conductor component may include a solid wire or ribbon comprising a noble metal. For example, the printed runner can comprise a pressure sensitive adhesive (PSA) with a conductor component. Exemplary noble metals include but are not limited to Pt, Au, Ru, or Ir. In some embodiments, the printed runner comprises a carbon runner that is non-porous and non-wettable with respect to the electrolyte. The printed runner includes a polymer adhesive that can be a welded polymer, a PSA, or another thermoset or UV cure that is inert with respect to the elements contained within the sensors. The adhesive seals to the carbon runner which is electronically conductive. It is desired that the sensor maintain this seal over the lifetime of the sensor, which can be months to decades.

The electrolyte layer may be a liquid or gel or solid or composite and is in electrolytic contact with the two or more electrodes of the electrode layer. In some embodiments, the electrolyte layer forms electrolytic contact with the electrode layer by impregnating the electrode layer, such as, for example, impregnating a wick that includes two or more electrodes coupled to the wick. By way of example only, the electrolyte layer may comprise phosphoric acid, sulfuric acid, aqueous phosphoric acid, aqueous sulfuric acid, methanesulphonic acid, aqueous phosphate salt solution, aqueous sulfate salt solution, potassium hydroxide, aqueous potassium acetate, lithium perchlorate in propylene carbonate, polyvinyl alcohol with sulfuric acid, polyacrylic acid, an ionic gel electrolyte, or ionic liquid. The electrolyte layer may comprise any suitable charge carrying entity that will also support the desired electrochemical reactions in the sensors and not create undesired reactions or conditions. Other suitable materials will be apparent to those of ordinary skill in the art in view of the teachings herein.

The electrolyte layer may have a substantially uniform thickness in the printed sensors, typically from about 1 mil to about 5 mils (125 microns). The electrolyte layer may include a matrix or gelling agent to prevent dryout or movement during vibration or use or otherwise enhance sensor properties. The electrolyte layer can cover at least a part of the sensing electrode area and the counter electrode in the sensor. That is, it is in electrolytic contact with the electrode layer, generally via an electrolyte reservoir formed on at least part of the electrode layer. The electrolyte layer may cover the entire electrode layer or the electrolyte layer may cover part of the electrode layer. The electrode layer may include a chamber adjacent to it to contain additional electrolyte or supporting material to enhance the lifetime or other performance of the electrolyte. In some embodiments, the electrode layer and the electrolyte layer are co-located such that the one or more electrodes are disposed within the electrolyte layer to facilitate electrolytic contact between the electrolyte and the one or more electrodes.

The encapsulation layer encapsulates the electrode and electrolyte layer forming an integrated structure with the porous substrate. The encapsulation layer essentially forms a housing structure with the porous substrate defining an internal region that comprises an electrode and electrolyte layer through which no material may enter or leave except through one or more access holes. The one or more access holes are designed to allow analyte access into and out of the housing structure. No material (except gases through the gas access port) can escape the inside of the sensor. This includes electrodes and electrolytes. The encapsulation layer may comprise polyimide, polycarbonate, polyethylene, polypropylene, polyisobutylene, polyester, polyurethane, polyacrylic, fluorine polymer, cellulosic polymer, fiberglass, polytetrafluoroethylene, any other non-reactive thermoplastic. The encapsulation layer may also comprise potting compounds, other materials or mixtures or composites thereof that can be suitably bonded to form the encapsulation. Other suitable materials will be apparent to those of ordinary skill in the art in view of the teachings herein. The encapsulation layer may have a substantially uniform thickness of from about 0.002 to 0.015 inches (2-15 mils) or any size that allows sufficient encapsulation of the sensor. The thickness and nature of the encapsulation and its placement depend upon the size of the sensor, the design of the sensor, and the processes used in the assembly.

The encapsulation layer may further comprise a capillary channel for entry into the electrolyte layer. Such design can expedite electrolyte filling and sensor assembly. The encapsulation layer may further comprise a gas vent hole, which allows air to exit the electrolyte reservoir as the electrolyte fills the reservoir. The gas vent hole may also allow venting in applications where there are large pressure fluctuations, for example, gas detection on airplanes or in submarines. By way of example only, the capillary channel and gas vent hole may be formed using plastic film stamping operations, laser cutting or die cutting to create contours and/or holes. The encapsulation should form and not close the gas access design to allow analyte entry as discussed above.

The printed sensor may further comprise a wicking layer that can serve as a separator or absorbent layer between the electrode layer and electrolyte layer. It can also serve as a material to wick the electrolyte into the sensor during production and hold the electrolyte against the electrodes. The wicking layer may be screen printed or inkjet printed onto all or a part of the electrode layer. The wicking layer may comprise silicates, silicon carbide, carbon, graphite, alumina, fiber glass, polymer, or other inert materials that can form a porous wick. The wicking layer may have a substantially uniform or variable thickness of from about 5 to 125 microns in the sensors herein but can be any suitable thickness that allows functionality of the wicking layer. In some embodiments, the electrolyte can impregnate the wicking layer to facilitate electrolytic contact between the one or more electrodes and the electrolyte. In some embodiments, the printed gas sensor does not include a wicking layer and the one or more electrodes are screen printed directly onto the porous substrate.

In some embodiments, the wick is not electrically conductive but forms an ionically conductive connection between the electrodes when flooded with ionically conductive electrolytes. When a reaction occurs at the electrode, the electrons and ions created in the electrochemical reaction are conducted by an electrolyte solution. The electrolyte solution can be free flowing or encompassed in a wick. Accordingly, in this exemplary embodiment, the wick is not ionically conductive, but the wick plus electrolyte structure in the sensor has ionic conductivity.

In some embodiments, the printed gas sensor is manufactured by the following method: printing two or more porous electrodes onto one side of a porous or partially porous substrate, curing the porous substrate, and bonding an encapsulation layer having a capillary channel to the porous substrate which encapsulates the two or more electrodes and forms an electrolyte reservoir. The method continues by filling the electrolyte reservoir with electrolyte through the capillary channel and sealing the capillary channel. In another embodiment, the printed gas sensor is manufactured by the following method: printing two or more porous electrodes onto one side of a porous or partially porous substrate, curing the porous substrate, printing or placing an electrolyte in the electrode area, and then bonding an encapsulation layer to the porous substrate, thereby encapsulating the two or more electrodes with electrolyte and forming an electrolyte reservoir. At this point the electrolyte reservoir is full. The method continues by sealing the entire chamber of electrodes and electrolyte with the gas access port being the only route for gas access. In further embodiments, the electrolyte reservoir can have a vent formed in it for exceptional pressure change applications. In each embodiment, the electrolyte and electrode chambers become sealed so that no electrode or electrolyte material can escape the encapsulation except through the access port in the same manner as analyte enters the printed gas sensor. In each embodiment, the access port can be sealed.

The method may further comprise forming a substrate layer from polytetrafluoroethylene, polyethylene, polypropylene, polyisobutylene, polyester, polyurethane, polyacrylic, fluorine polymer, cellulosic polymer, fiberglass, a mixture thereof, or any other non-reactive thermoplastic or bondable polymer. The substrate layer may be formed by laser cutting, die cutting, stamping, roll milling, or other film forming processing.

The method may further comprise forming an encapsulation layer from polytetrafluoroethylene, polyethylene, polypropylene, polyisobutylene, polyester, polyurethane, polyacrylic, fluorine polymer, cellulosic polymer, fiberglass, a mixture thereof, or any other non-reactive thermoplastic polymer or inert single or dual mixture epoxy type encapsulation compounds. The encapsulation layer may be formed by molding, laser cutting, die cutting, stamping, or other suitable processes.

An ink composition is used to print the two or more electrodes onto one side of a porous substrate. As mentioned above, the ink composition used to print the electrode layer (i.e., two or more porous electrodes) may comprise: from about 60% to about 90% of a catalyst, from about 10% to about 50% of polymer particles (e.g., micron-sized Teflon particles), less than about 10% of a binder, less than about 10% of a surfactant and from about 0% to about 10% of one or more modifiers. The catalyst can comprise noble metals like Pt or Pd or alloys or supported catalysts like Pt on carbon or other supports as such formulations are well known in the art. Printing may be done by screen printing, gravure, inkjet printing, stenciling, or other suitable printing technology known in the art that may be used in accordance with the teachings herein. In a screen printing process, the printing screen may comprise stainless steel wire, a plastic mesh, or a platinum mesh across a screen frame. The mesh size may vary depending upon the desired print film thickness, and hence the thickness of the printed two or more electrodes. The area to be screen printed may be patterned on the screen using a desired electrode design template. A squeegee may then be used to spread ink over the screen and the desired pattern is printed on a porous substrate. In an inkjet printing process, it is desired that the formula of the ink be controlled so that the ink remains printable for some time on the screen and does not dry too fast. The added retardant should control this process and one exemplary embodiment herein uses a PVA/water solution as the retardant or modifier additive to the metal-plastic ink composite formula.

The method may further comprise a curing step where the sensor ink and porous substrate may be cured by heating or drying at about 100° C.-200° C., such as, for example at 150° C. for about 10 minutes in an oven. Further curing when using PTFE may require additional heating to about 280° C. to 300° C. for about one hour to form a suitable cured and porous diffusion electrode for gaseous reactions. The curing step may be used to remove any solvent present. Remaining solvent not removed during this step may cause problems by polluting the atmosphere surrounding the sensor element. Curing may be performed by, for example, forced air drying (e.g., at elevated temperatures), infrared irradiation, ultraviolet irradiation, ion-beam irradiation, gamma irradiation, and combinations thereof. The curing step is chosen to fix the electrode structure in the remaining composite porous or partially porous electrode. In one exemplary embodiment for CO, for example, the mixture of PTFE particles (30%) and Pt particles (60%) and ethylcellulose (10%) is cured at 300° C. for one hour to create a CO electrode having a useable porosity and hydrophilicity/hydrophobicity for measurement of CO in air at 0.1-10,000 ppm. Other electrode embodiments will be described in more detail below, including electrodes formed from a PTFE catalyst ink suspension, dry PTFE powder, polypropylene powder, or polyethylene powder. Other exemplary electrodes formulations include ink prepared with 3.125 wgt % ethyl cellulose plus 1.25 wgt % PVA.

The method may further comprise printing a wicking layer onto the two or more electrodes and/or porous substrate. Printing of the wicking layer may be accomplished by screen printing or inkjet printing using a slurry of ink comprising particulate wick material. As mentioned above, the particulate wick material may comprise silicates, silicon carbide, carbon, graphite, fiberglass, fiberglass filter paper, or other porous materials or fibrous materials that when matted together form pores or wickable substrates. In these embodiments, the wick materials should not be electrically conductive. The wicking ink may also comprise silica-based filter paper that is ground or mashed into small particles and mixed with water or water with an added salt, acid or base. The composition has sufficient water and vehicle (e.g. PVA, ethyl cellulose or other retardant) to make an ink suitable for printing.

In some embodiments, the wicking layer may also include an electrolyte material such as a salt (e.g., $H_2SO_4$), acid, base, or the like. The electrolyte material can be a dry material and can be activated into a liquid electrolyte through exposure to a solvent, such as water vapor. The dry electrolyte material can allow the printed gas sensor to be assembled dry, for example in a dry box, without the need for wet electrolyte addition. Any gas access areas (holes, porous regions, or the like) can be covered by a removable adhesive, such as a sticker, to seal the printed gas sensor from any gas entry. When the electrolyte material is exposed to air, the vapor in the air can enter the printed gas sensor and mix with electrolyte material to fill the printed gas sensor with liquid electrolyte. This can be accomplished by removing the removable adhesive, for example, when the printed gas sensor is positioned for use.

The bonding of an encapsulation layer or substrate layer may comprise thermal bonding, chemical bonding, adhesive bonding, ultrasonic bonding, lamination, pressure bonding, o-ring bonding or welding. Once the encapsulation layer is bonded to the porous substrate thereby forming an electrolyte reservoir, the electrolyte reservoir is filled. Filling may be done by submerging the capillary channel or the entire printed sensor in electrolytic solution. As the capillary channel or printed sensor is submerged, electrolytic solution rises through the capillary channel and into the electrolytic reservoir. Once inside the reservoir, the wicking layer, if present, may capture some of the electrolyte thereby holding it against the electrode. After the reservoir is filled, the capillary channel and any vent holes may be sealed by, for example, thermal sealing, chemical sealing, adhesive sealing (e.g., epoxy). When wicking is used, a vent is desired for the air to flow out and this should also be sealed at the end. This seal can be potting materials or a gas porous vent to be used for equalization of pressure when the sensor is used for pressure change applications.

The resulting printed gas sensor may be of various sizes and dimensions. For example, the thickness of the printed gas sensor may be less than about 1000 micron (about 1 mm). In embodiments of the printed gas sensor further comprising a filter layer and a reservoir overflow layer, the thickness is about 3000 microns (about 3 mm). We have constructed prototype sensors where the total thickness of all layers is about 500 microns thick. Current prototypes have a surface area of about 1 mm$^2$ to about 9 mm$^2$ and a thickness of about 0.5 mm to 1 mm. Because silk screen resolution is continuously improving, smaller sensors may be possible with the approach described herein.

The gas sensor performance of the exemplary CO electrodes demonstrated herein may have a measurement range of from about 0 ppm to about 1000 ppm CO. In another example, the gas sensor performance for CO may have a measurement range from about 0 ppm to about 500 ppm. The measurement output signal from the screen-printed CO electrode in the gas sensor may range from about 1 nano-amps/ppm to about 25 nanoamps/ppm. The measurement output signal from the gas sensor may also range from about 10 nanoamps/ppm to about 25 nanoamps/ppm. These signals are range selectable by choosing the size of the gas access port and can be reduced with smaller holes for gas access. Even smaller signals (e.g., 10-100× smaller) are possible and can be amplified using currently available electronics. The printed gas sensor may produce a measurement response time of less than about 30 seconds at 20° C. The printed gas sensor may also produce a measurement response time of less than about 20 seconds at 20° C. Thinner sensors can produce faster response times because diffusion times decrease over shorter diffusion distances. For example, electrolyte volumes herein still produce a very stable sensor even under conditions of near 0% RH for a long time giving this printed sensor a long lifetime of CO monitoring in field use.

In one exemplary embodiment for CO monitoring, the printed gas sensor electrochemically senses gases using an electronic circuit called a potentiostat. In the potentiostatic method or mode, the gas to be quantitatively sensed or detected may contact the sensing or working electrode in the presence of an electrolyte and generate a current that is proportional to the amount of target gas entering the cell. The common or counter electrode can run the complementary half-cell reaction. The reference electrode operating in a potentiostatic circuit can maintain the thermodynamic potential of the working electrode during sensing. Simple electronics may be interfaced to the sensor to convert the current to a voltage and amplify the voltage for meter or recorder readout.

Turning to the figures, FIGS. 1-3 depict an example of a printed gas sensor operable to detect and measure carbon monoxide levels. Of course, other target gases that may be detected and/or measured using the printed gas sensor will be apparent to those of ordinary skill in the art in view of the teachings herein. Further, while exemplary geometries have been disclosed, other geometries will be possible to those of ordinary skill in the art. In addition, while exemplary combinations of ink properties (viscosity, composition, drying rate, etc.) and ink structure (thickness, porosity, etc.) have been disclosed for the exemplary sensors, one of ordinary skill in the art can envision other inks and compositions and properties and structures. While exemplary combinations of these specially designed parts with the printing processes and assembly processes have been disclosed, alternatives will become obvious to those skilled in the art for the design and assembly of a family of related electrochemical gas sensors by this new approach that combines the many special features of materials and processes described herein.

Referring now to FIG. 1, an exemplary version of printed gas sensor 100 is shown. The printed gas sensor 100 shown comprises: a porous substrate 200, an electrode layer 300, a liquid or gel electrolyte layer 400 in electrolytic contact with the electrode layer 300, and an encapsulation layer 500 that encapsulates the electrode layer 300 and electrolyte layer 400 thereby forming an integrated structure of a printed gas sensor 100 with the porous substrate 200. It should be understood that FIG. 1 is a schematic depiction of the printed gas sensor 100 and is not to scale. For example, the electrode layer 300 is not severed by the encapsulation later 500. In some embodiments, passes underneath the encapsulation layer 500 and is partially pushed into the surface of the porous substrate 200. In other embodiments, encapsulation layer 500 is sealed to electrode layer 300 to create a fluid tight seal. In this example, the substrate layer 200 comprises porous polytetrafluoroethylene, though other porous materials may be used with porosity desirably in the region 205 for gas access, and has four electrodes shown printed onto one side of the porous polytetrafluoroethylene substrate 200. If porous PTFE is used, the porosity can be filled with adhesive or a back-plate or similar approach as long as porosity remains in the desired gas access area, 205. The porous PTFE is a convenient substrate for the gas sensor electrode but can be difficult for printing. The substrate layer 200 has an access port 205 for entry of a gas sample to be measured, and an optional filter 215 covering the access port 205 can be made of virtually any shape and size to enhance sensor operation in applications. Also illustrated in FIG. 1 is an optional backplate 220. The backplate may comprise a TFE substrate, or other plastic and can be utilized to block gas access to the entire substrate 200 except for an opening corresponding to the access port 205. This layer 220 is illustrated not to scale and can be very thin in nature or just fill the pores totally or partially in layer 200.

Figure 2A:
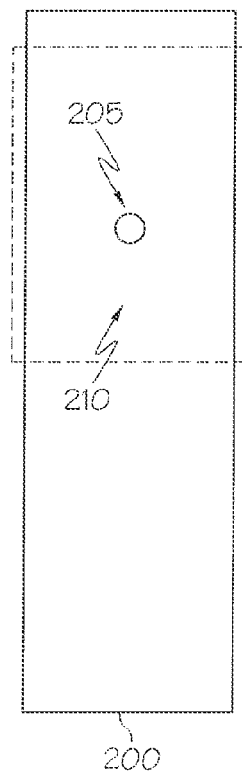
FIGS. 2A & 2B depict a substrate layer of the exemplary printed sensor shown in FIG. 1.
Figure 2B:
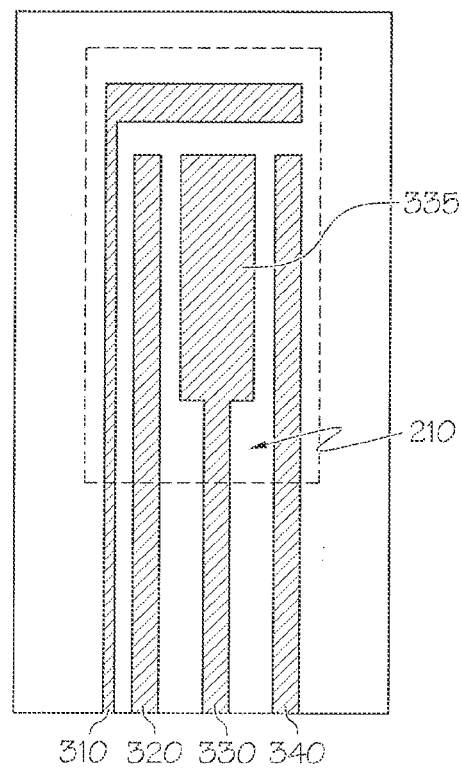

As further depicted in FIGS. 2A & 2B, the electrode layer 300 is shown having a test electrode 310, reference electrode 320, working (or sensing) electrode 330 and counter electrode 340 formed on one side of the porous substrate 200, the side opposite to the gas access and optional filter. It should be understood that, like other components and features described herein, test electrode 310 and reference electrode 320 may be omitted entirely if desired or not needed by the sensing system. The substrate layer 200 also depicts the area 210 to be encapsulated by the encapsulation layer 500. The electrolyte layer 400 is within the encapsulation layer 500 and adjacent to and in electrolytic contact with the electrode layer 300.

The test electrode 310 may allow the printed gas sensor to self-test for degradation or failure of the working electrode 330 (and therefore, the ability of the printed gas sensor 100 to accurately sense and measure a target gas concentration) and be aware of sensor condition. The test electrode 310 may be arranged to sense a gas normally present in the atmosphere, e.g., oxygen, to detect the decomposition of the electrodes or electrolyte or provide added temperature compensation capability or similar performance enhancements over time. The test electrode 310 may also be arranged to generate a test gas within the sensor and in a controlled amount to effect a test of the operation of the sensor (i.e., working electrode 330). The test electrode 310 may comprise a catalyst comprising Pt, Pd, Au, Ag, Ru, ruthenium dioxide, Cr, Mn, Fe, Co, carbon, or combinations or alloys or composites suitable to the need and function in the sensor. The test electrode 310 can also be electrically pulsed, for example during gas generation, electronic sensor testing, or the like.

In this example, the working electrode 330 has a sensing area 335 and is comprised of a platinum metal catalyst composite for CO sensing, though other metal catalysts may be used as disclosed above for CO or for other gas sensors. The reference electrode 320 may be comprised of Pt composite, Ag/AgCl, Pb/PbO2, or other material suitable to the sensor design. In this particular example for a CO sensor, Pt-black composite is used. The counter electrode 340 may be comprised of Pt, Au, Pb/PbO2, or any suitable material for the particular sensor. In this particular example, a CO sensor with Pt-Black and Teflon particle composite is used.

The electrolyte layer 400 is in electrolytic contact with the electrode layer 300 and comprises lithium perchlorate in propylene carbonate or alternatively polyvinyl alcohol with sulfuric acid or sulfuric acid in a porous glass or porous plastic matrix. The electrolyte can use ionic liquids or solid polymers or other electrolytes known in the sensor system arts, such as, for example fuel cells and batteries. The electrolyte layer 400 covers the sensing area 335 of the working electrode 330 and extends to the other sensor electrodes such that all electrodes in the sensor are in electrolytic contact (i.e. in contact through the electrolyte). In some cases, it may also be desirable for the thin film electrolyte to be in contact with an electrolyte reservoir 410 formed on or over the electrode layer 300 and it may be formed in a section of the encapsulation layer. The electrolyte reservoir 410 may include an expansion area 410A to house electrolyte that expands from the electrolyte reservoir 410 when electrolyte reservoir 410 is full, such as when the volume of the electrolyte expands in a high relative humidity environment.

The encapsulation layer 500, as shown in FIG. 1, encapsulates the electrode 300 and electrolyte layer 400 thereby forming an integrated structure with the porous substrate 200. As further depicted in FIG. 3A, encapsulation layer 500 comprises a capillary channel layer 510 having a capillary channel 520 for entry of the electrolyte layer. Capillary channel layer 510 also defines a bucket volume 515 where electrolyte can reside during expansion from accumulated moisture from the air. The capillary channel layer 510 is an optional component to the operation of the sensor The encapsulation layer 500 may further comprise a cap layer 530 having a gas vent hole 540, as depicted in FIG. 3B. The gas vent is useful for filling the electrolyte in one exemplary embodiment and for applications wherein the sensor is used and the pressure is changed of the sensed ambient at a certain rate. The capillary channel layer 510 may further include one or more capillary channel access ports 510A that allow electrolyte to flow through the capillary channel layer 510. The capillary channel layer 510 and cap layer 530 shown were laser cut from polypropylene be formed using plastic film stamping operations in this example, laser cutting or die cutting to create contours and/or holes. The two layers are packaged together by heat sealing them together or alternatively by adhesive bonding, and then the two layer package is heat sealed or otherwise bonded to the porous substrate layer 200. It is desired that the electrode or a conductor emerge through the encapsulation so that external contact to the electrodes encapsulated within is made. The connection means can be by conductor wire, conductive plastic, printed runner, pre-metalized plastic, or any material that is a conductor and can be sealed such that the electrode and electrolyte materials cannot escape from the sensor over many years of use. The cap layer 530 also depicts the area 535 to be encapsulated and sealed, using, for example, a heat seal or a PSA. While the encapsulation layer is shown having two sub-layers, it should be understood that the encapsulation layer may comprise one layer having a capillary channel, bucket volume, and gas vent or any other optional feature formed therein. Pre-forming these features should save assembly time and cost in manufacture.

FIGS. 4-7 depict another example of a printed gas sensor operable to detect and measure carbon monoxide levels. Referring to FIG. 4, an exemplary version of a printed gas sensor 1000 is depicted. The printed gas sensor 1000 shown may measure carbon monoxide levels; however, other target gases may be used. Sensor 1000 comprises: a porous substrate 1100; an electrode layer 1200; a wicking layer 1300, a liquid or gel electrolyte layer 1400 in contact and permeating the wick 1300 and in electrolytic contact with the electrode layer 1200; and an encapsulation layer 1500 that encapsulates the electrode layer 1200, wicking layer 1300, and electrolyte layer 1400 thereby forming an integrated structure with the porous substrate 1100.

As further depicted in FIG. 5, the substrate layer 1100 comprises porous PTFE, though other porous materials may be used, and has a gas access hole 1105 where the porosity of the PTFE is maintained and everywhere else can be closed off either by a substrate plastic bonded to it or by additives painted on it. The substrate layer 1100 further comprises a filter 1115, depicted in FIG. 4, covering the gas access hole which can be a plastic part used to close off the porous PTFE from the ambient everywhere except the gas access part. Note that the gas access part is preferred to align with the working electrode printed on the opposite side of the porous PTFE. The substrate 1100 is further shown in FIG. 6 having four electrodes printed onto it. The electrode layer 1200 is shown having a test electrode 1210, reference electrode 1220, working (or sensing) electrode 1230 and counter electrode 1240 formed on one side of said porous substrate 1100. As mentioned above, test electrode 1210 and reference electrode 1220 may be omitted entirely if desired. The substrate layer 1100 also depicts the area 1110 to be encapsulated by the encapsulation layer 1500.

In this example, the working electrode 1230 has a sensing area 1235, and is comprised of a platinum metal catalyst, though other metal catalysts may be used as disclosed above. The counter electrode 1240 may be comprised of Pt-black-PTFE porous electrode composite in this particular example also for a CO sensor to result.

The wicking layer 1300 of exemplary printed sensor 1000 is shown in FIG. 4. The wicking layer 1300 may be screen printed or inkjet printed onto the electrode layer 1200. The wicking layer 1300 may comprise silicates, Nafion, silicon carbide, carbon, graphite, glass fiber filter paper, porous polypropylene, and Teflon. The wicking layer 1300 may also comprise other battery separator type materials that will wick and hold electrolyte against the electrodes in the sensor; such materials are typically chosen to be compatible with the electrolyte. In this embodiment, the wick may not be electrically conductive and may be wettable by the chosen electrolyte.

As depicted in FIG. 4, the electrolyte layer 1400 is in electrolytic contact with the electrode layer 1200 and comprises lithium perchlorate in propylene carbonate or alternatively polyvinyl alcohol with sulfuric acid, polyethylene oxide and lithium chloride, ionic liquids, acetic acid with certain salts or KCl or sodium, potassium or cesium hydroxide solutions. The electrolyte layer 1400 covers the sensing area 1235 of the working electrode 1230. That is, it provides electrolytic contact with the electrodes in the electrode layer 1200, and generally via an electrolyte reservoir 1410 which is an empty, unfilled portion of the electrolyte layer formed within the encapsulation area 1500. In one further embodiment, an electrode contact area 1250 is outside the encapsulation area 1500 wherein electronic contact is made to the electrodes.

The encapsulation layer 1500, as shown in FIG. 4, encapsulates the electrode layer 1200, wicking layer 1300, and electrolyte layer 1400 thereby forming an integrated structure with the porous substrate 1100 through which no materials can pass over long times. The encapsulation layer 1500, as further depicted in FIG. 7, comprises a capillary channel 1510, a bucket volume 1520 and a gas vent hole 1530. In this embodiment, the capillary channel layer 1510 and bucket volume 1520 shown are formed from polypropylene using a plastic film stamping operation to create the contours. The gas vent hole is laser cut. The encapsulation layer 1500 is heat sealed to the porous substrate layer 1100. These features allow for convenient filling with electrolyte solution but are not required if the wicking layer already contains the electrolyte or the electrolyte is placed over the electrodes before encapsulation steps are taken.

Figure 8:
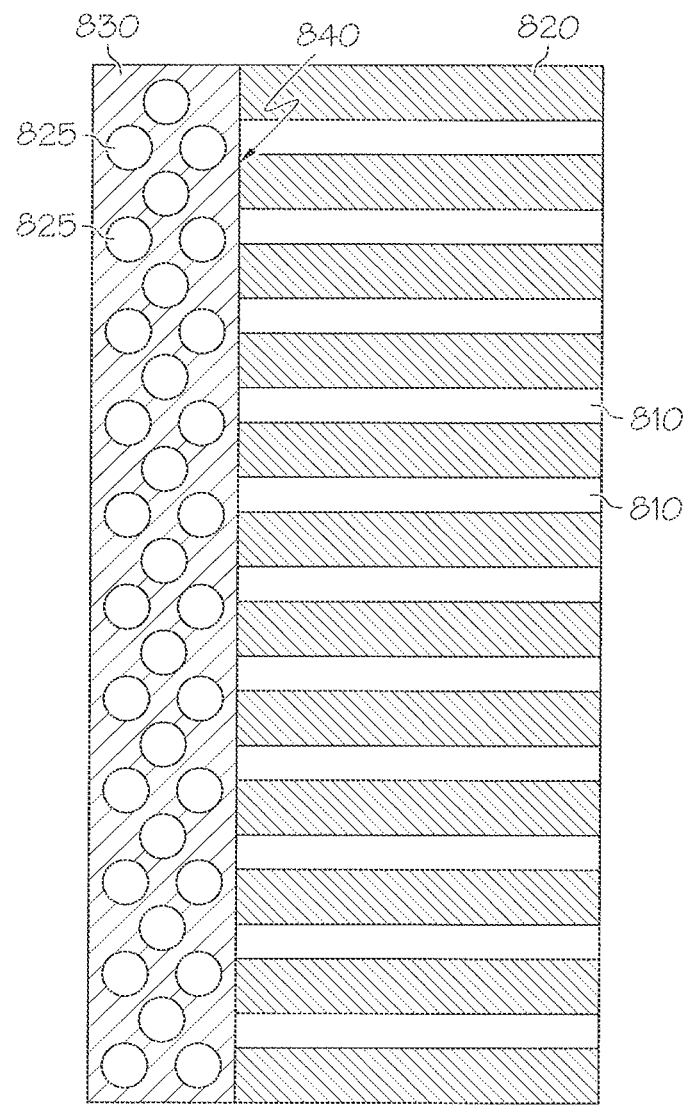
FIG. 8 depicts an exemplary electrochemical reaction in the porous gas electrode.

Referring to FIG. 8, the electrochemical reaction zone for a gaseous analyte that has been created in the exemplary sensors of FIGS. 1-3 and 4-7 is depicted. The carbon monoxide electrochemical reaction takes place in the working electrode at the triple phase boundary 840 of the metal catalyst (surface of the working electrode), the electrolyte (touching the surface of the working electrode), and the gas also arriving at and touching the surface of the electrode and electrolyte and perhaps being considered dissolved in the electrolyte in the triple phase boundary region. As shown in FIG. 8, the carbon monoxide gas 810 enters through the gas access hole and through the pores of a porous PTFE substrate 820 and contacts the catalyst particles 825 that are at least partially wetted with electrolyte 830. It should be understood that FIG. 8 is a schematic depiction of the electrochemical reaction zone for a gaseous analyte and is not to scale. As such, in some embodiments, the catalyst particles 825 are in physical contact such that electricity can be conducted through the catalyst particles 825.

Figure 9:
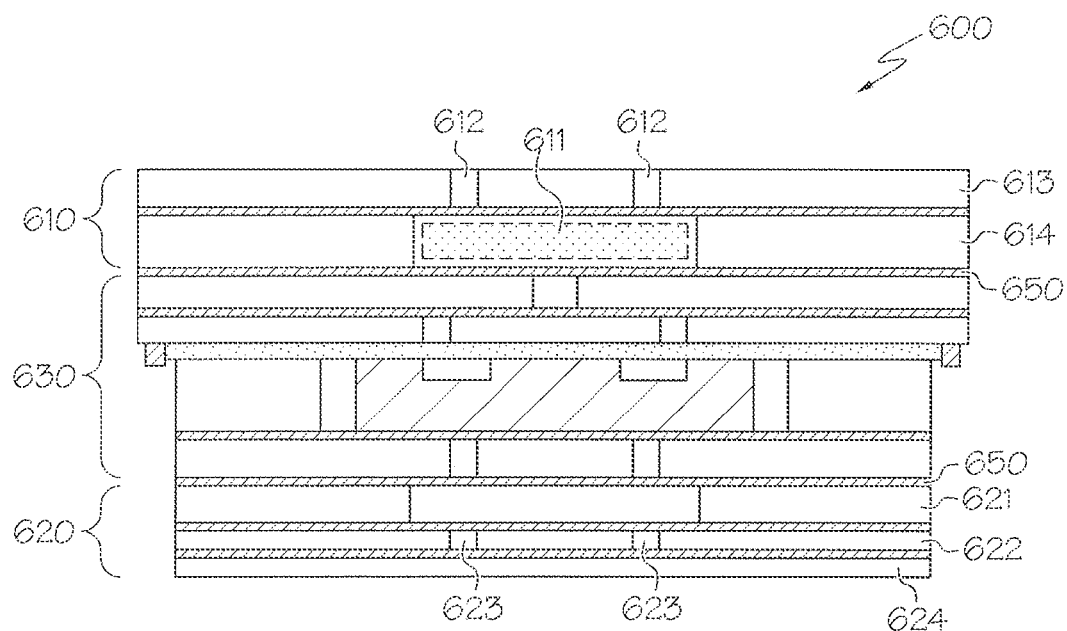
FIG. 9 depicts an exemplary version of a printed gas sensor.
Figure 10:
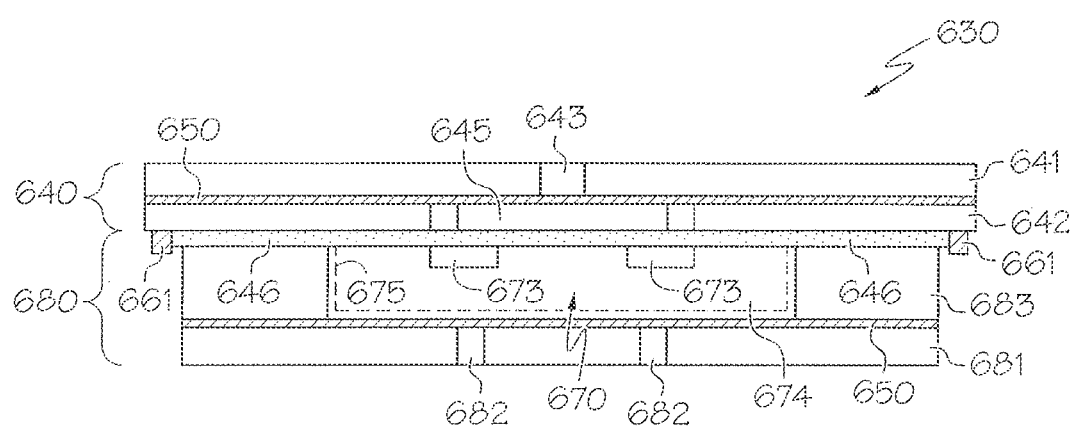
FIG. 10 depicts an exemplary version of a printed gas sensor.

Referring now to FIGS. 9 and 10, an exemplary version of a printed gas sensor 600 is shown. The printed gas sensor 600 comprises a sensor layer 630 coupled to a filter assembly 610 on a first side of the sensor layer 630 and a reservoir assembly 620 on a second, opposite side. The sensor layer 630 comprises a substrate layer 640 coupled to an encapsulation layer 680 using a PSA 650. This forms an integrated structure and defines an electrolyte cavity 675 located between the substrate layer 640 and an encapsulation layer 680. One or more electrodes 673 are coupled to a wick 670 (FIG. 10) positioned within the electrolyte cavity 675. The substrate layer 640 can be coupled to the filter assembly 610 and the encapsulation layer 680 can be coupled to the reservoir assembly 620.

In some embodiments, the printed gas sensor 600 includes a filter assembly 610 comprising a fill port layer 613 and a filter cavity ring 614. The fill port layer 613 comprises formed plastic or other suitable materials, such as, for example, PET and includes one or more filter holes 612 for gas entry into the filter assembly 610. The filter cavity ring 614 comprises carbon or other suitable materials, such as, for example a combination of 300 LSE and PET. The filter cavity ring 614 is coupled to the fill port layer 613 using PSA 650 on a first side of the filter cavity ring 614 and coupled to the substrate layer 640 using PSA 650 on a second, opposite side of the filter cavity ring 614. The PSA creates a hermetic seal, preventing gas entry into the sensor layer 630 or the filter assembly 610 at any location except the one or more filter holes 612.

When the fill port layer 613 is coupled to the filter cavity ring 614 a cavity is formed below the fill port layer 613 and within the filter cavity ring 614. Filter material 611 can be located within this cavity. The filter material 611 may permit access of certain target gases, such as, for example, CO and prevent access of certain gases, such as, for example $H_2S$, $HO_2$, $SO_2$, $O_2$, $NO_2$, HCl. The filter material 611 may comprise a $C/KMnO_4$ plug chemically configured to remove $H_2S$, $HO_2$, $SO_2$, $O_2$, $NO_2$, HCl, condensable hydrocarbons, alcohols, or the like. The $C/KMnO_4$ plug may include carbon cloth, activated carbon, or other filter materials impregnated with $KMnO_4$ or other reactive materials. The reactive materials can be designed to prevent entry of interfering gases while allowing entry of target gases, or analytes. Alternately, the filter material 611 may comprise a carbon and $KMnO_4$ on alumina mixture, or other carbon mixtures. In operation, gases can enter the filter holes 612 at the top of the fill port layer 613 and reach the filter material 611. Any gas that is able to travel through the filter material 611 (e.g., CO) can enter the sensor layer 630 of the printed gas sensor 600. In some embodiments, the printed gas sensor 600 does not include a filter assembly 610. In these embodiments, gases can enter directly into the sensor layer 630.

Still referring to FIG. 9, the printed gas sensor 600 may include a reservoir assembly 620 coupled to the sensor layer 630 opposite the filter assembly 610. The reservoir assembly 620 can function as an overflow chamber for electrolyte 674 disposed within the electrolyte cavity 675 of the sensor layer 630. Environmental factors, such as relative humidity, may cause the electrolyte 674 and other liquids to expand within the electrolyte cavity 675. The reservoir assembly 620 allows some of the expanded electrolyte 674 and other expanded fluids within the printed gas sensor 600 to flow into the reservoir assembly 620 without breaking the hermetic seals located throughout the printed gas sensor 600. To accommodate electrolyte 674 expansion, the volume of the reservoir assembly 620 can be between three and six times larger than the volume of the electrolyte layer 675, for example, when the electrolyte 674 comprises 4M $H_2SO_4$. This fill volume allows the printed gas sensor 600 to accommodate fluid expansion that can occur when the printed gas sensor 600 is used in high relative humidity conditions, such as a 95% relative humidity environment.

The reservoir assembly 620 may comprise a reservoir fill port layer 622 having one or more reservoir overflow holes 623 and a reservoir cavity ring 621. The reservoir fill port layer 622 comprises formed plastic or other suitable materials, such as, for example, PET. The reservoir cavity ring 621 comprises formed plastic or other suitable materials, such as, for example a combination of 300 LSE and PET. The reservoir cavity ring 621 is coupled to the reservoir fill port layer 622 on a first side of the reservoir cavity ring 621 and coupled to a sensor layer 630 on an opposite side of the reservoir cavity ring 621. The one or more reservoir overflow holes 623 in the reservoir fill port layer 622 allow an electrolyte 674 to access the electrolyte cavity 675 (FIG. 10) of the sensor layer 630 through the reservoir assembly 620. Once electrolyte 674 enters electrolyte cavity 675, the reservoir overflow holes 623 can be hermetically sealed or plugged, preventing liquids or gases from entering the sensor layer 630 except through gas access regions 643 (FIG. 10). In some embodiments, the reservoir assembly 620 further comprises a reservoir plug 624 coupled to the reservoir fill port layer 622, opposite the reservoir cavity ring 621. The reservoir plug 624 can hermetically seal the reservoir overflow holes 623. In some embodiments, the reservoir plug 624 is coupled to the reservoir fill port layer 622 after the electrolyte 674 has filled the electrolyte cavity 675. In some embodiments, the reservoir cavity ring 621 and the reservoir fill port layer 622 are integral forming an integral overflow chamber or "bucket".

Referring now to FIG. 10, sensor layer 630 of the printed gas sensor 600 of FIG. 9 is depicted in more detail. The sensor layer 630 comprises a substrate layer 640 having a first partially porous substrate 641 and a second partially porous substrate 642, coupled together using PSA 650 disposed on substantially the entire surface of the first partially porous substrate 641 facing the second partially porous substrate 642. The first partially porous substrate 641 comprises polycarbonate and the second partially porous substrate 642 comprises LSE and PET. In other embodiments, the first partially porous substrate 641 and the second partially porous substrate 642 may comprise other formed plastics, such as PTFE. The first partially porous substrate 641 comprises gas access regions 643 that allows gas, for example a target gas, to enter the sensor layer 630. Gas access regions 643 may be holes. Gas access regions 643 may also be porous regions in the first partially porous substrates 641 formed by selectively coating the first partially porous substrate 641 with polyimide. Regions of the first partially porous substrate 641 covered with polyimide block gas access and regions of first partially porous substrate 641 without polyimide form gas access regions 643 to allow gases including one or more target gases to enter the sensor layer 630. The second partially porous substrate 642 may comprise a slot 644 configured such that a PTFE disk 645 can be disposed within the slot 644. The slot 644 is located substantially coaxial with the gas access regions 643 and may have a diameter larger than the diameter of the gas access regions 643 such that when a PTFE disk 645 is positioned within the slot 644 it couples to a portion of the first partially porous substrate 641 overhanging the slot 644 and is substantially coaxial with the gas access regions 643. The PTFE disk 645 may comprise a partially porous PTFE membrane such as, for example, MuPore. Gas that enters the sensor layer 630 through the gas access regions 643 diffuses through the PTFE disk 645 and reaches the electrodes 673 positioned within the electrolyte cavity 675. It should be understood that the substrate layer 640 may alternatively comprise a single partially porous substrate including one or more gas access regions and further including a slot for housing a PTFE disk.

The substrate layer 640 can further comprise a printed runner 646 printed directly onto the second partially porous substrate 642. The printed runner 646 faces the electrolyte cavity 675 and comprises a non-porous hydrophobic material that does not soak up any electrolyte 674. The printed runner 646 can be stamped, vapor deposited, or the like, onto the second partially porous substrate 642. The printed runner 646 is patterned, allowing it to engage with a variety of electrodes 673 within the electrolyte cavity 675. In some embodiments, the printed runner 646 comprises one or more conductive traces having conductive ink.

Still referring to FIG. 10, an encapsulation layer 680 comprises an electrolyte fill port layer 681 with one or more electrolyte access holes 682 coupled to an encapsulation cavity ring 683. The electrolyte fill port layer 681 and the encapsulation cavity ring 683 comprise formed plastic, such as PET or a combination of LSE and PET. The encapsulation cavity ring 683 is further coupled to the second partially porous substrate 642 opposite the electrolyte fill port layer 681. PSA 650 is disposed between the electrolyte fill port layer 681, the encapsulation cavity ring 683 and the second partially porous substrate 642 of the substrate layer 640, hermetically sealing the encapsulation layer 680 and forming an electrolyte cavity 675 within the encapsulation cavity ring 683. The electrolyte cavity 675 can house an electrolyte 674 and a wick 670 coupled to one or more electrodes 673. In some embodiments, the electrolyte fill port layer 681 and the encapsulation cavity ring 683 form a single integral, "bucket" structure which is coupled to the second partially porous substrate 642 and houses the electrolyte cavity 675. The electrolyte access holes 682 in the electrolyte fill port layer 681 allow electrolyte 674 to enter the electrolyte cavity 675.

The sensor layer 630 depicted in FIG. 10 further comprises one or more electrodes 673 coupled to a wick 670. The wick 670 can comprise porous glass fiber or glass fiber filter paper. In this embodiment, the one or more electrodes 673 are screen printed, inkjet printed, stamped, or stenciled onto the wick 670. Electrodes 673 can be printed and cured onto the wick 670 before the wick 670 is assembled into the printed gas sensor 600. For example, the wick 670 can be embedded with electrode 673 creating a wick-electrode assembly having three regions. A first region includes only wick 670, a second region includes electrode 673 embedded in the wick 670, and a third region includes only electrode 673, extending above the wick 670. The second region is graded such that it contains gradually more electrode 673 when measured from a boundary with the first region (comprising only wick 670) to the boundary with the third region (comprising only electrode 673). This transition from wick 670 to electrode 673 facilitates the intimate contact and transition of electrolyte 674 through the wick 670 to the electrode 673, encouraging wetting. Further, the wick-electrode assembly creates a strong structural bond between the electrode 673 and the wick 670.

The glass fiber or a glass fiber filter paper of the wick 670 can tolerate higher temperatures than the materials of the substrate layer 640 or the encapsulation layer 680. For example, the wick 670 can tolerate a curing temperature of about 300° C. This allows the one or more electrodes 673 to be cured onto the wick 670 before being assembled into the printed gas sensor 600. The wick 670 is also compressible. In some embodiments, the height of the electrolyte cavity 675 is less than the initial height of the wick 670. When the wick 670 is assembled within the electrolyte cavity 675, the wick 670 is compressed to fit within the electrolyte cavity 675.

The one or more electrodes 673 may comprise PTFE ink mixed with metal catalyst and additives to form a PTFE ink black composite electrode. In particular, the one or more electrodes 673 may comprise 1.44-1.45 g Pt, 0.16±0.1 g graphite carbon and 0.80-0.81 g Teflon suspension (0.48 g PTFE). The Teflon suspension can be a mixture of TFE particles less than 1 μm diameter, water, surfactant, and 3 mL ethyl cellulose solution. In some embodiments, the electrodes 673 are printed from inks that are prepared from dry PTFE particles instead of an aqueous PTFE solution. In other embodiments, the electrodes 673 are printed from inks that are prepared from polypropolyne powder or polyethylene powder, as explained in more detail below.

Referring still to FIG. 10, the wick 670 with one or more electrodes 673 are positioned within the electrolyte cavity 675. Once the wick 670 is assembled into the electrolyte cavity 675, electrodes 673 that are positioned on the wick 670 can mate with the printed runner 646. When an electrolyte 674, such as $H_2SO_4$, is introduced into the electrolyte cavity 675 it contacts the wick 670. The electrolyte 674 can seep into the wick 670 and contact the electrode 673. Once the electrolyte 674 and electrode 673 are in contact, and a target gas, such as CO enters the printed gas sensor 600 through the gas access regions 643, an electrochemical reaction is generated in the electrolyte cavity 675. The electrochemical reaction between the electrode 673, the electrolyte 674, and a target gas generates an electric current in the printed runner 646 and sends electric signal to one or more circuits connected to the printed runner 646 at one or more electrical contact points 661. This electric signal communicates to one or more circuits that a target gas is detected in the printed gas sensor 600.

Referring still to FIG. 10, a printed runner 646 faces the wick 670 and contacts at least one electrode 673, and extending along a length of the printed runner 646. Alternative embodiments may include two or more printed runners 646. The printed runner 646 terminates at one or more electrical contact points 661 coupled to the outer portion of the printed runner 646. The electrical contact points 661 facilitate an electrical connection between the printed runner 646 and one or more circuits, conductive wires, or the like. This allows electrical current generated by an electrochemical reaction between the electrode 673, electrolyte 674, and a target gas to travel along the printed runner 646, from the electrode 673 to one or more circuits. The one or more circuits may be arranged on a printed circuit board. The one or more circuits can use the electrical current generated by the electrode 673, electrolyte 674, and target gas to trigger a signal or an alarm function. In alternative embodiments, the substrate layer 640 may not comprise a printed runner 646. In this embodiment, a printed runner 646 is coupled to the partially porous substrate facing the wick 670. In some embodiments, printed runner 646 comprises one or more conductive traces having conductive ink.

Figure 11A:
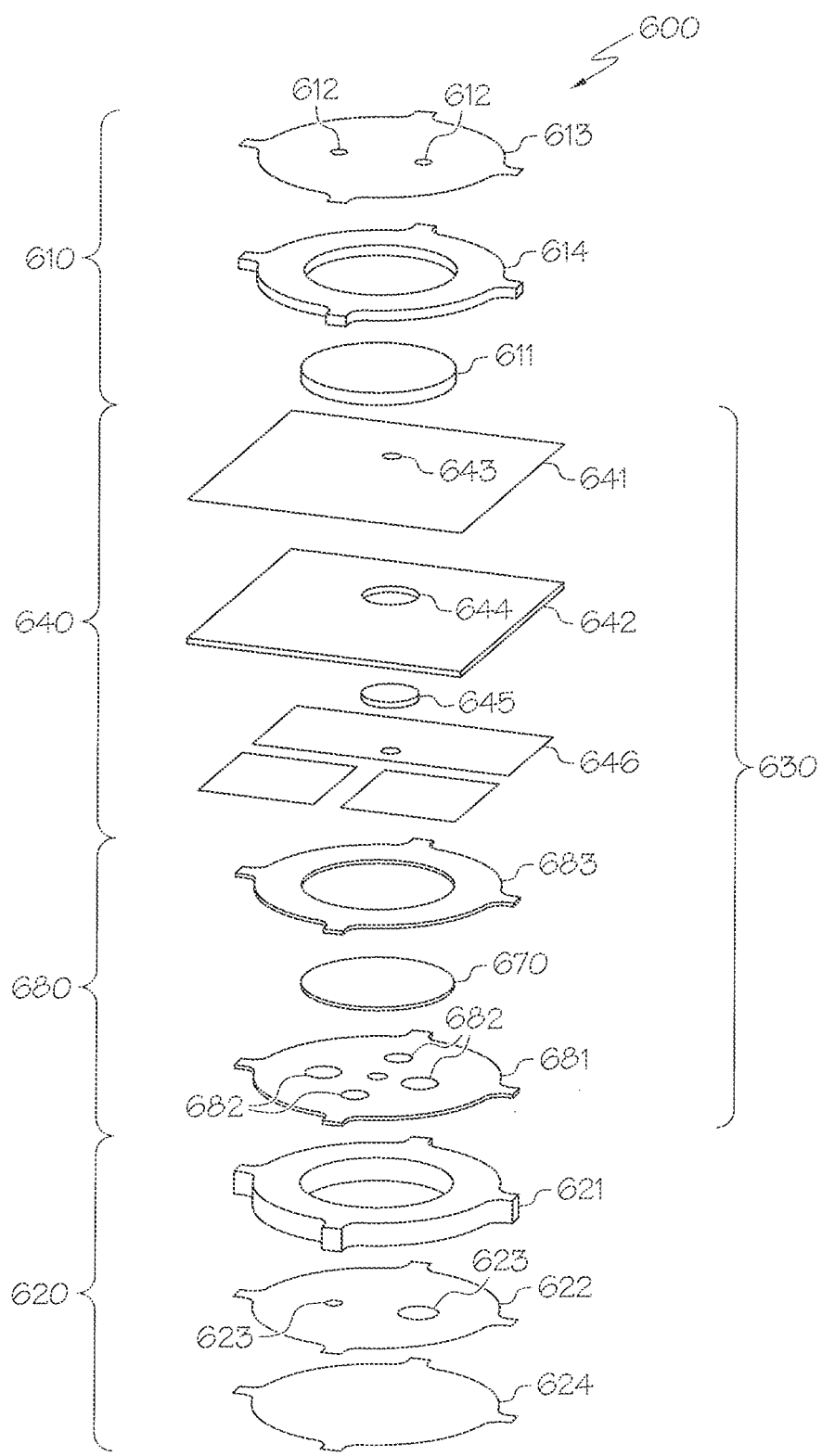
FIG. 11A depicts an exploded view of the printed gas sensor of FIG. 9.
Figure 11B:
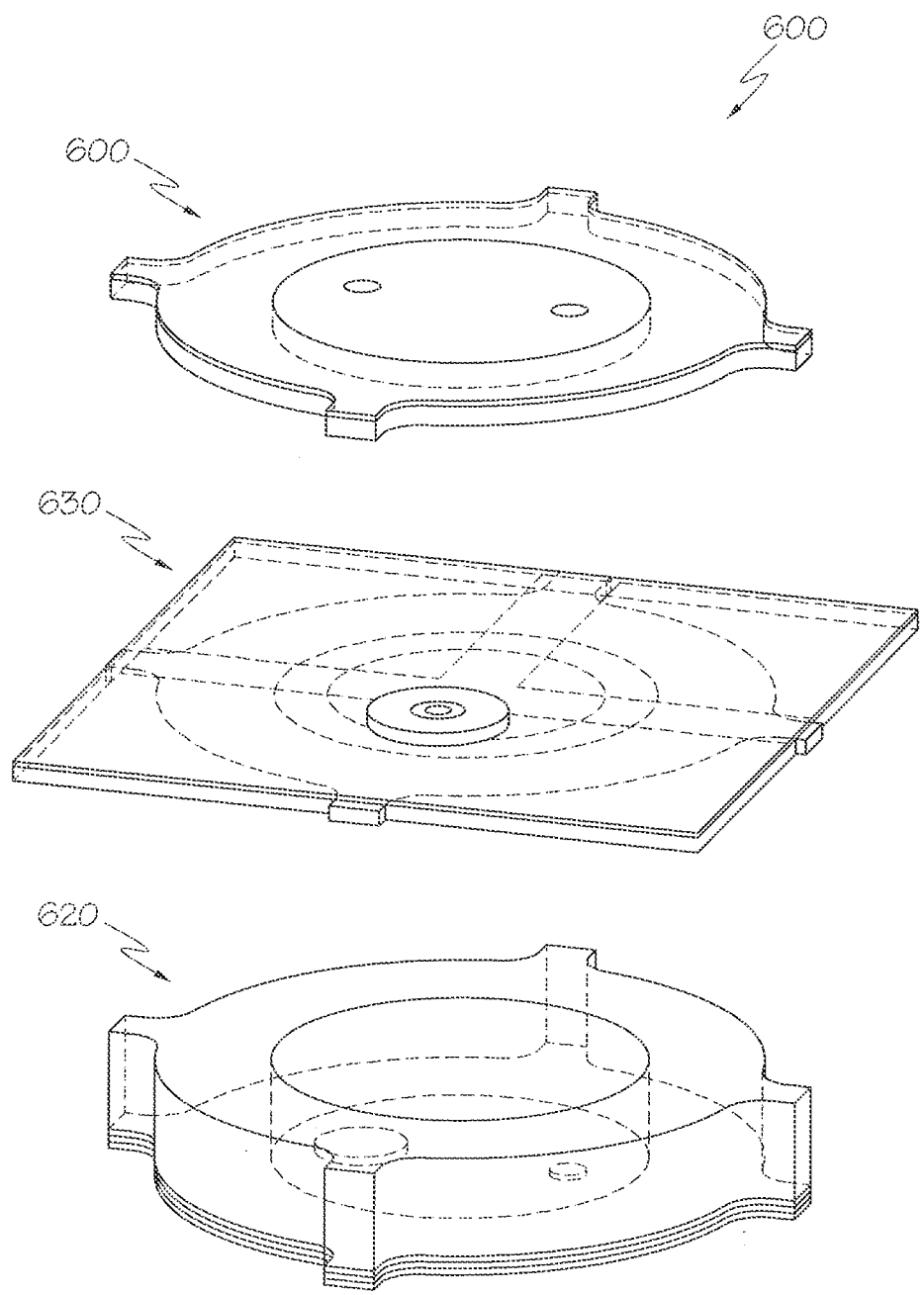
FIG. 11B depicts a partially assembled view of the printed gas sensor of FIG. 9

Referring now to FIG. 11A, the embodiments of FIGS. 9 and 10 are depicted in an exploded view. Referring now to FIG. 11B, the filter assembly 610, reservoir assembly 620, and sensor layer 630 of FIGS. 9 and 10 are depicted in printed form. While FIGS. 11A and 11B depict the optional filter assembly 610 and optional reservoir assembly 620, it should be understood that embodiments of the printed gas sensor 600 without a filter assembly 610 or a reservoir assembly 620 are contemplated.

Figure 12:
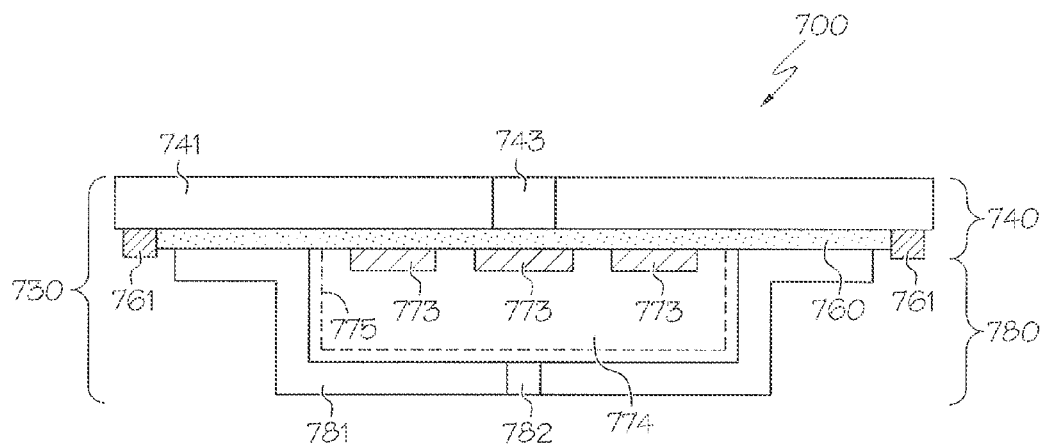
FIG. 12 depicts an exemplary version of a sensor layer of a printed gas sensor.

Referring now to FIG. 12, a sensor layer 730 of an embodiment of a printed gas sensor 700 comprising one or more electrodes 773 curable at temperatures lower than the melting point and deformation point of the materials of the sensor layer 730 is depicted. The sensor layer 730 comprises a solid substrate 741 coupled to an encapsulation housing 781 forming an electrolyte cavity 775 between the solid substrate 741 and the encapsulation housing 781. The solid substrate 741 can be partially porous to allow gas to enter the printed gas sensor 700. Gas access regions 743 can be formed by selectively coating the solid substrate 741 with polyimide. Regions of the solid substrate 741 covered with polyimide block gas access and regions of the solid substrate 741 without polyimide form gas access regions 743 to allow gases including one or more target gases to enter the sensor layer 730. The gas access regions 743 can also be one or more holes. The solid substrate 741 is also hydrophobic and oligophobic to prevent electrolyte from absorbing into the solid substrate 741 and blocking the gas access regions 743. The encapsulation housing 781 includes one or more encapsulation holes 782. The solid substrate 741 and the encapsulation housing 781 comprise low temperature plastics such as polycarbonate substrate and PET substrate. Polycarbonate substrate and PET substrate are chemically inert and have melting points less than or equal to 260° C. Further, one or more printed runners 760 are coupled to the solid substrate 741 and are configured to carry electric current generated in the electrolyte cavity 775 to one or more contact points 761. The one or more contact points 761 can be in electrical contact with one or more circuits, such as, for example, a printed circuit board.

In the embodiment depicted in FIG. 12, one or more electrodes 773 are printed directly on the solid substrate 741. The electrodes 773 are made from ink compositions which cure at temperatures below the melting point or deformation point of both the solid substrate 741 and the encapsulation housing 781. This allows the entire sensor layer 730 to undergo the curing process for the electrode 773 without melting the solid substrate 741 or the encapsulation housing 781. One exemplary low temperature electrode ink composition is a polypropolyne mixture comprising polypropolyne, catalyst, solvent, and additives, such as, for example, platinum, palladium, or alloys or supported catalysts like platinum on carbon. Another exemplary electrode ink composition comprises polyethelene, catalyst, solvents, and additives, such as, for example, platinum, palladium, or alloys or supported catalysts like platinum on carbon. These electrode ink compositions cure at temperatures less than or equal to 250° C. and can form porous gas diffusion electrodes that are partially hydrophobic. Further, electrodes 773 printed from these electrode ink compositions form a triple phase boundary with an electrolyte 774 and a target gas. When an electrolyte 774 contacts an electrode 773 a contact angle of 70° or greater is formed, partially wetting the electrode 773. For example, an electrolyte 774 comprising $H_2SO_4$ may have a contact angle of 75° or greater. The printed gas sensor 700 depicted in FIG. 12 may further comprise a filter assembly and a reservoir assembly coupled to the sensor layer at opposite sides of the sensor layer. The filter assembly and the reservoir assembly may be the same or substantially similar to the embodiments depicted in FIG. 9.

Figure 13:
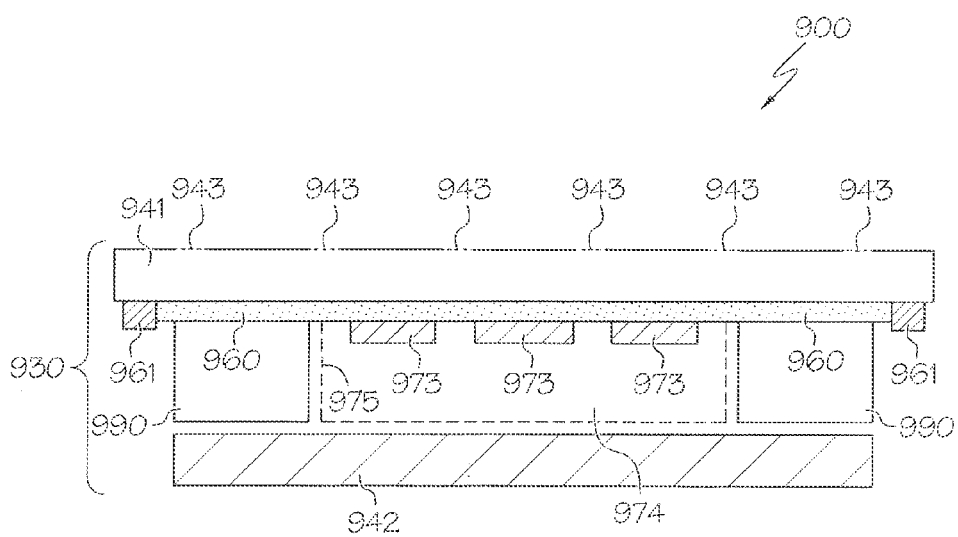
FIG. 13 depicts an exemplary version of a sensor layer of a printed gas sensor.

Referring now to FIG. 13, a sensor layer 930 of an exemplary printed gas sensor 900 is shown. Sensor layer 930 comprises a high temperature upper substrate 941 partially coated with polyimide to form one or more porous gas access regions 943. Regions of the high temperature upper substrate 941 covered with polyimide block gas access and regions of the high temperature upper substrate 941 without polyimide form gas access regions 943 to allow gases including one or more target gases to enter the sensor layer 930. In some embodiments, gas access regions 943 may comprise one or more holes. The high temperature upper substrate 941 is coupled to a high temperature lower substrate 942 using one or more sealer spacers 990, forming an electrolyte cavity 975 between the high temperature upper substrate 941 and the high temperature lower substrate 942. The sealer spacers 990 are a solid material that can be used to weld the high temperature upper substrate 941 to the high temperature lower substrate 942 using a thermoplastic welding rod or other exemplary plastic welding method. During this welding process, the material of the sealer spacer 990 is selectively melted and can seep into the pores of the high temperature upper substrate 941 and the high temperature lower substrate 942; gluing, welding, or otherwise fastening the high temperature upper substrate 941 and the high temperature lower substrate 942 together. This forms a hermetic seal and creates the electrolyte cavity 975 between the high temperature upper substrate 941 and the high temperature lower substrate 942. In some embodiments, the high temperature upper substrate 941, the high temperature lower substrate 942, or both can be partially porous. This partial porosity can be formed by pattering each substrate 941, 942 with a photoresist material using a UV masking process.

The high temperature upper substrate 941 and the high temperature lower substrate 942 may comprise PTFE, polyimide, or any other high temperature, chemically inert material and the sealer spacers 990 may include FEP or other chemically inert, flowable bonding material that can withstand corrosive chemicals used in electrolytes, electrodes, and analytes and can withstand temperatures of 260° C. or higher. The materials of the high temperature upper substrate 971, high temperature lower substrate 972, and sealer spacers 990 can withstand curing temperatures of at least 260° C. For example, polyimide can withstand temperature of up to about 400° C. and PTFE can withstand temperatures of up to about 330° C. These high temperature materials allow the sensor layer 930 to be assembled onto a circuit board during circuit board production and placed in a solder reflow furnace at 260° C. for various periods of time, for example, nine seconds.

One or more electrodes 973 are coupled to the high temperature upper substrate 941 using inkjet or screen printing techniques and are positioned within the electrolyte cavity 975. The one or more electrodes 973 may comprise TFE bonded electrodes curable at temperatures from about 260° C. to about 330° C., such as, for example, 300° C. The electrodes may comprise PTFE ink, a metal catalyst, solvents, and additives. Some electrodes 973 may be configured to interact with the electrolyte 974 and a target gas to create an electrochemical reaction and generate an electrical current. Other electrodes operate as a bunny tester or a conductivity tester. An electrode 973 operating as a conductivity tester may be configured to continuously or intermittently check whether the cell is functioning properly and may measure and monitor the concentration of the electrolyte 974. In some embodiments, multiple electrodes 973 may be configured to each detect different target gases. For example, a first electrode 973 can detect CO and a second electrode (not shown) can detect gases such as $H_2S$, $O_3$, $SO_4$, or $NO_2$. The electrolyte cavity 975 can be partially filled with a wick that contacts each electrode 973 and wets each electrode 973 with electrolyte 974. Further, in embodiments in which electrolyte 974 comprises $H_2SO_4$, the volume of the electrolyte 974 can expand or contract depending on the relative humidity of the environment surrounding the printed gas sensor 900. The volume of a fixed amount of electrolyte 974 can expand three to six times in volume in a high relative humidity environment. As described in more detail above, the reservoir assembly coupled to the sensor layer 930 can be configured to house overflow electrolyte.

Still referring to FIG. 13, the hermetically sealed electrolyte cavity 975 houses the one or more electrodes 973 and the electrolyte 974, creating a location for electrochemical reactions between the electrode 973, the electrolyte 974, and the target gas. The materials of the high temperature upper substrate 941, high temperature lower substrate 942, and sealer spacers 990, such as, for example, PTFE, can be chemically inert; allowing any electrolyte 974 to enter the electrolyte cavity 975 without generating a chemical reaction between the materials of the high temperature upper substrate 941, the high temperature lower substrate 942, and the electrolyte 974. Exemplary electrolytes 974 include corrosive acids, bases, and salts, such as, for example, $H_2SO_4$, which can withstand curing temperatures up to 340° C. Other exemplary electrolytes 974 include solvents and RTILs, such as, for example, ionic liquids which can withstand curing temperatures up to 360° C.

Still referring to FIG. 13, printed runners 960 are coupled to the high temperature upper substrate 941, facing the electrolyte cavity 975. The printed runners 960 are configured to carry electric current generated in the electrolyte cavity 975 to one or more contact points 961. The one or more contact points 961 can be in electrical contact with one or more circuits, such as, for example, a printed circuit board. The printed runners 960 can be compositionally and functionally the same as those described above with respect to FIGS. 10 and 12. The printed gas sensor 900 may further comprise a filter assembly and a reservoir assembly coupled to the sensor layer at opposite sides of the sensor layer 930. The filter assembly and the reservoir assembly may be the same or substantially similar to the embodiments depicted in FIG. 9.

The diameter of a gas inlet hole of any of the embodiments described above may be varied to alter the sensitivity range of target gas detection in the sensor layer. In each embodiment, the amount of gas entering the sensor should match the reactivity of the sensor. As the gas inlet hole diameter increases, more catalyst should be present in the electrode to optimize the signal to noise ratio of the printed gas sensor. For example, a gas inlet hole with a diameter of 1 mm can be matched with a 5-10 mg WE catalyst and a 0.25 mm gas inlet hole can be matched with a 2.5 mg catalyst. The specific sensitivity and signal to noise ratio can be selected based on the detection range and output requirements of the printed gas sensor. For example, a high target gas detection range is between about 0 ppm and about 1000 ppm and a low target gas detection range is between about 0 ppm and about 10 ppm. A printed gas sensor with the low target gas detection range will have less catalyst and a smaller gas inlet hole than a printed gas sensor with the high target gas detection range. Target matching creates scaled sensitivity levels in the printed gas sensors. For example, a printed gas sensor with a low target gas detection range can detect low levels of target gas in part because it can minimize background noise. Also, a printed gas sensor with a high target gas detection range can detect high levels of target gas while tolerating high levels of background noise.

In the embodiments described herein, the electrolyte acid concentration can be selected to match the relative humidity of the environment in which the printed gas sensor will be used. For example, if the relative humidity of the environment is greater than 95% continuous (e.g., coal mines) then about a 1M acid electrolyte should be used. If relative humidity of the environment is less than 10% (e.g., dry city gas), then about a 10M acid electrolyte should be used. In some embodiments, a single sensor design can operate in a relative humidity environment ranging from 5-95% relative humidity. In these embodiments, the printed gas sensor can further include the reservoir assembly coupled to the sensor layer of the printed gas sensor. An environment with variable relative humidity can cause the electrolyte to expand and contract. By including the reservoir assembly, the electrolyte can expand and contract into and out of the reservoir assembly without breaking the hermetic seal of the sensor layer. In some embodiments, the reservoir assembly should have a volume multiple times larger than the electrolyte cavity. For example, when the electrolyte is $H_2SO_4$, the volume of the reservoir assembly can be three to six times greater than the volume of the electrolyte cavity.

In some embodiments, porous electrodes comprise alternative polymer components. In some embodiments, the electrodes comprise dry PTFE particles which replace the standard PTFE aqueous dispersion particles. In some embodiments, the electrodes are prepared with polypropylene particles replacing the standard PTFE aqueous dispersion particles. In other embodiments, polyethylene particles replace the standard PTFE particles. One advantage of replacing the PTFE with the polymers noted above is the electrodes will cure at lower temperatures. This allows direct printing of the electrodes onto the plastic substrates and parts. The electrodes can be cured onto the plastic substrates and parts during the assembly process. Special handling or pick and place operations are not required. This can reduce and simplify the processing steps.

In any of the embodiments described above, the manufacturing process of the printed gas sensors can be scalable, for example, in bulk sheets comprising 10-100 printed gas sensors per sheet, such as, for example, a sheet with 60 printed gas sensors. In some embodiments, the scalable manufacturing process can produce the printed gas sensors of the various embodiments in one or more sheets that can be a variety of sizes. For example, printed as sensors can be manufactured in 2×5 sheets comprising 10 printed gas sensors, 5×5 sheets comprising 25 printed gas sensors, 10×10 sheets comprising 100 printed gas sensors, or any other size and shape of scalable, manufactured sheet. It should be understood that the process of manufacturing printed gas sensors can be scaled to any size desired, such as sheets having 500 printed gas sensors, 1000 printed gas sensors, or more.

In some embodiments, the electrodes are prepared with an ethyl cellulose solution. In this embodiment, 5 g 10 cP ethylcellulose is dissolved into a 75 mL isophorone 25 mL diacetone alcohol solution. The solution is dissolved by stirring in a covered container overnight at 50° C. to 75° C. In some embodiments, the 75 mL isophorone is replaced with 75 mL octanol which reduces the toxicity and the odor. Other solvents such as nonanol or decanol can also be used to replace isophorone in the ethyl cellulose solution. The solvent must have at least the minimum polarity required to dissolve the diacetone. In a preferred embodiment, the solvent evaporates at a slow pace. In some embodiments, ethyl cellulose can be added to adjust the viscosity for printing. In a preferred embodiment, the dispersion is stable with a low evaporation rate and good viscosity. When the electrode is cured (typically between 60° C. and 250° C., at a temperature that does not damage the plastic substrate) the solvent must leave the composite electrode behind.

In some embodiments, the electrodes comprise a catalyst ink suspension of 23-25% weight PTFE. More specifically, the catalyst ink suspension comprises a mixture of 1.44-1.45 g Pt, 0.16±0.01 g graphite carbon and a 0.80-0.81 g PTFE suspension comprising 0.48 g PTFE particles less than 1 μm, water, surfactant, and 3 mL ethyl cellulose solution or octanol solution.

Figure 14:
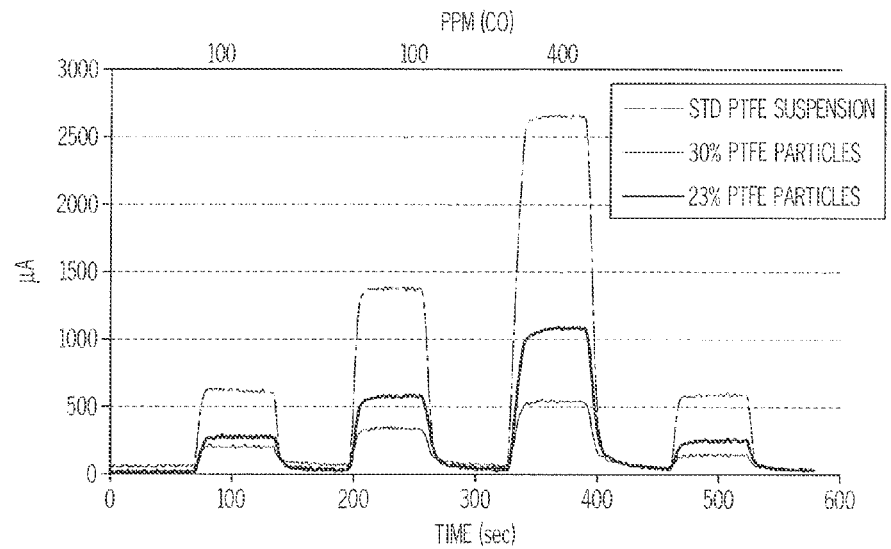
FIG. 14 graphically depicts the response signal of electrodes comprising dry PTFE particles and electrodes comprising a PTFE aqueous solution.

In some embodiments, inks are prepared from dry PTFE particles instead of a standard PTFE aqueous solution. Dry PTFE particles are prepared from dry PTFE powder and are suspended directly into the solvent. They are not placed in an aqueous suspension like the standard PTFE suspension. Electrodes prepared from dry PTFE particles yield 20-45% of the response of electrodes prepared using a PTFE aqueous solution. FIG. 14 illustrates the response signal in μAmps of electrodes comprising 23% and 30% dry PTFE particles and electrodes comprising a PTFE aqueous solution. The signal peaks are measuring, from left to right in FIG. 14, the addition of 50 ppm target gas, 100 ppm target gas, and 400 ppm target gas, respectively.

In some embodiments, electrodes are prepared using low temperature binders such as polypropylene and polyethylene powders. These powders are hydrophobic binders. The densities of polypropylene (PPRO) and polyethylene (PE) are lower than the density of PTFE. (PTFE=2.0-2.2 g/cc; PPRO=0.93 g/cc; PE=0.97 g/cc). Because of the lower density, the optimized weight percentage for PPRO and PE is lower than PTFE (15-17 wgt % PPRO, PE vs. 23-25 wgt % PTFE).

In some embodiments, the PPRO catalyst ink suspension comprises a mixture of 1.44-1.45 g Pt (74-78 wgt %), 0.16±0.01 g graphite carbon (8-9 wgt %), 0.25-0.30 g PPRO powder (14-17 wgt %) and a 3 mL ethyl cellulose solution. The response of electrodes prepared with 5-7 μm PPRO particles is about 10-20% of the response of electrodes prepared with PTFE aqueous solution. In some embodiments, the PE catalyst ink suspension comprises a mixture of 1.44-1.45 g Pt (74-78 wgt %), 0.16±0.01 g graphite carbon (8-9 wgt %), 0.25-0.30 g PE powder (14-17 wgt %) and a 3 mL ethyl cellulose solution. The response of electrodes prepared with 2-4 μm PE particles is about 25-30% of the response of electrodes prepared PTFE aqueous solution.

Figure 17:
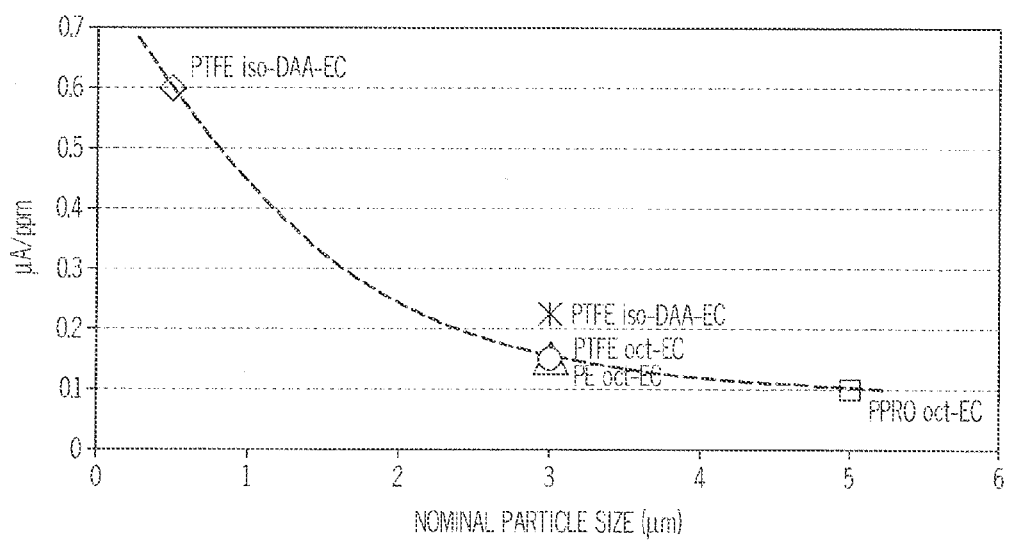
FIG. 17 graphically depicts results of CO signal vs. polymer particle size.
Figure 18:
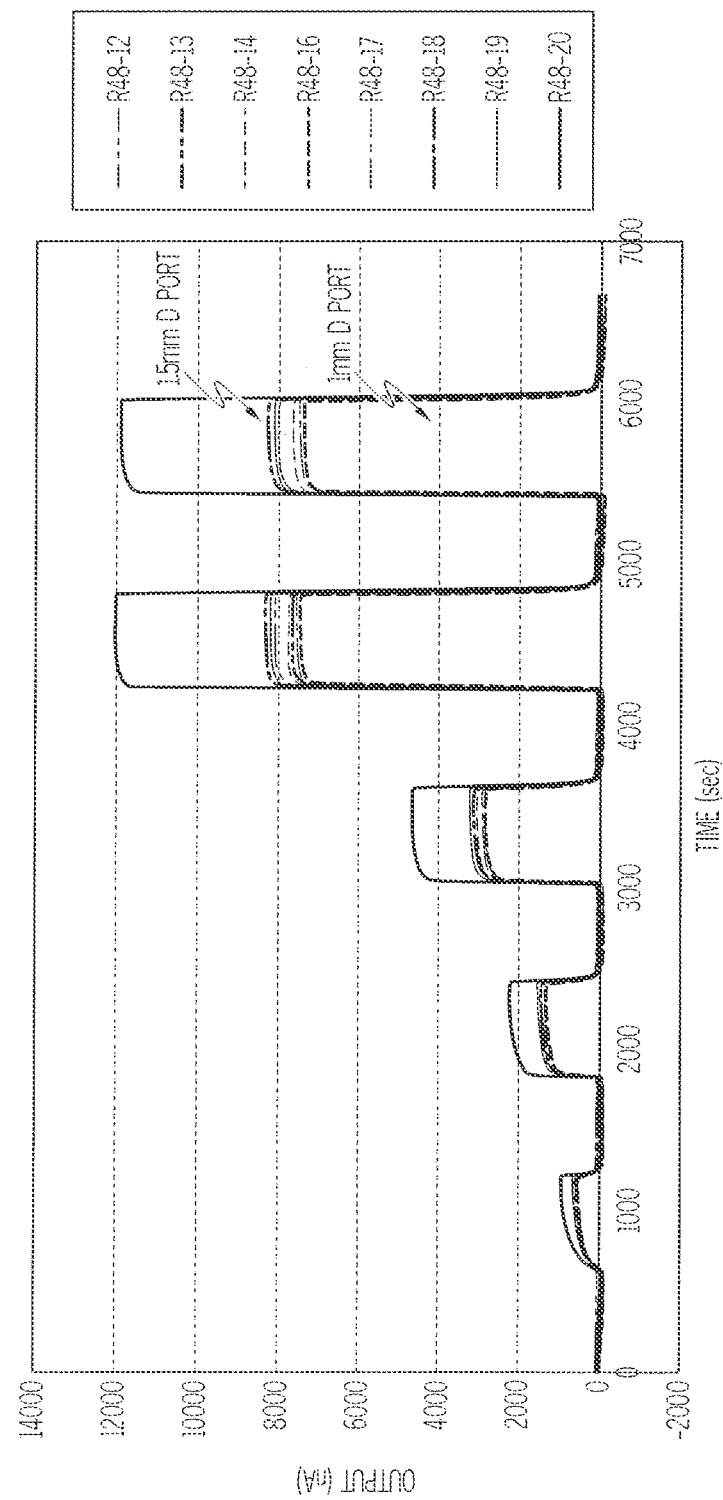
FIG. 18 graphically depicts a relationship between gas port size and sensor to sensor consistency.

In some embodiments, electrode sensitivity can be optimized by reducing the catalyst particle diameter. FIG. 17 illustrates the effect of polymer particle diameter on the sensitivity of electrodes comprising 17-23 wgt % polymer and 77-83 wgt % Pt, measuring signal per ppm (μA/ppm) over nominal polymer particle diameter (μm). CO sensitivity is independent of the specific polymer, provided the requirements for a proper triple phase boundary are met, but depends on the size of the particles. For example, smaller particles increase CO sensitivity. In some embodiments, sensor-to-sensor performance can be optimized by reducing the gas inlet hole diameter. In one example, by reducing the gas inlet diameter from 1.5 mm to 1.0 mm, the sensor-to-sensor variation was improved, as illustrated in FIG. 18. In some embodiments, a reduction in gas port area from 3 $mm^2$ to 1 $mm^2$ reduces the signal by a factor of around 2.5-3.0 (from 50 nA/ppm to 20 nA/ppm) and also reduces the amount of background noise that can enter the sensor. Both signal and noise can decrease linearly with catalyst area. As the perimeter to area ratio of the gas port area is increased, there is an improvement in the signal to noise ratio. The sensitivity of a printed gas sensor can be optimized by matching the gas inlet hole diameter with the size of the electrode layer. For example, a printed gas sensor with a gas inlet hole having a 0.5 mm diameter can be optimized with a 5-7 mil thick electrode layer having a 3 mm diameter and a 2.5 mg/$cm^2$ catalyst.

While several devices and components thereof have been discussed in detail above, it should be understood that the components, features, configurations, and methods of integrating and using the devices discussed are not limited to the unique contexts provided above. In particular, components, features, configurations, and methods of use described in the context of one of the devices may be incorporated into or out of any of the other devices. Furthermore, not limited to the further description provided below, additional and alternative suitable components, features, configurations, and methods of fabricating and using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

EXPERIMENTS

In the following experiments, alternative polymer components were used in the formation of porous gas electrodes. Catalytic ink suspensions comprising different polymer components were used to create electrodes. These electrodes were tested and measured. In particular, experiments were preformed in which the standard PTFE aqueous dispersion in the catalytic ink suspension was replaced with dry PTFE particles, polypropylene particles and polyethylene particles, respectively. Experiments were also performed with the goal of optimizing CO sensitivity, optimizing sensor to sensor performance, and improving a sensor's signal to noise ratio.

The standard PTFE catalyst ink suspension comprises a mixture of 1.44-1.45 g Pt, 0.16±0.01 g graphite carbon and a 0.80-0.81 g PTFE suspension comprising 0.48 g PTFE particles less than 1 μm, water, surfactant, and 3 mL ethyl cellulose solution or octanol solution. The ethyl cellulose solution is a combination of 5 g 10 cP ethyl cellulose mixed with a solution comprising 75 mL isophorone and 25 mL diacetone alcohol that is stirred in a covered container on a hot-plate overnight at 50-70° C. to dissolve the solution. To form the standard PTFE catalyst ink suspension, the Pt, graphite carbon, PTFE, ethyl cellulose, water, and surfactant are mixed using sonication, dispersed onto the wick or substrate using a screen printing or stenciling process, then cured. When the standard PTFE catalyst ink suspension is cured, the solvent will evaporate, leaving the composite electrode behind. It should be understood that any of the embodiments of the catalyst ink suspension described herein can be formed into electrodes through the process of sonicating the catalyst ink suspension, dispersing the catalyst ink suspension onto the wick or substrate using a screen printing or stenciling process, then curing the catalyst ink suspension.

The ethyl cellulose solution can also be formed using octanol, nonanol, or decanol in place of isophorone. Octanol is less toxic and less odorous than isophorone. The solvent used can have a small amount of polarity to dissolve the diacetone and should not evaporate too quickly. The solvent can also take up some of the additive ethyl cellulose to adjust the viscosity for printing. This can result in stable dispersion, low evaporation rate, and good viscosity.

Experiment 1

In experiment 1, the catalyst ink suspension was prepared from dry PTFE powder instead of the standard PTFE suspension (TFE-30™ PTFE) to determine the difference in response between electrodes made with dry and aqueous PTFE catalyst inks. The catalyst ink suspension formed with dry PTFE powder comprises a mixture of 1.44-1.45 g Pt (67-71 wgt %), 0.16±0.01 g graphite carbon (7-8 wgt %), and 0.48-0.49 g PTFE powder (22-25 wgt %) combined with 3 mL ethyl cellulose solution. The particle diameter of dry PTFE powder is about 1-5 μm. This is larger than the particle diameter of the standard PTFE suspension, which has particles no larger than 1 μm. FIG. 14 illustrates the response signal in μAmps of electrodes comprising 23% and 30% dry PTFE particles and electrodes comprising a PTFE aqueous solution. The signal peaks are measuring, from left to right in FIG. 14, the addition of 50 ppm target gas, 100 ppm target gas, and 400 ppm target gas, respectively. As illustrated in FIG. 14, electrodes formed with a catalyst ink suspension comprising dry PTFE powder yield 20-45% of the response of electrodes prepared with a standard PTFE suspension. The lower sensitivity of dry PTFE appears to be related to the particle diameter. This size to sensitivity relationship is expanded upon in experiment 4, below.

Experiment 2

In experiment 2, the catalyst ink suspension was prepared from polypropylene (PPRO) powder (a hydrophobic binder) instead of PTFE. PPRO binds at a lower temperature than PTFE. The PPRO powder particles used were about 5-7 μm. The optimized weight percentage of PPRO powder is lower than PTFE because PPRO has a lower density than PTFE. The density of PTFE is 2.0-2.2 g/cc and the density of PPRO is 0.93 g/cc. The optimized weight percentage of PTFE is 23-25 wgt % and the optimized weight percentage of PPRO is about 15-17 wgt %. The catalyst ink suspension formed with PPRO powder comprising a mixture of 1.44-1.45 g Pt (75-79 wgt %), 0.16±0.01 g graphite carbon (8-9 wgt %), 0.25-0.30 g PPRO powder (14-17 wgt %) combined with a 3 mL ethyl cellulose solution.

Figure 15:
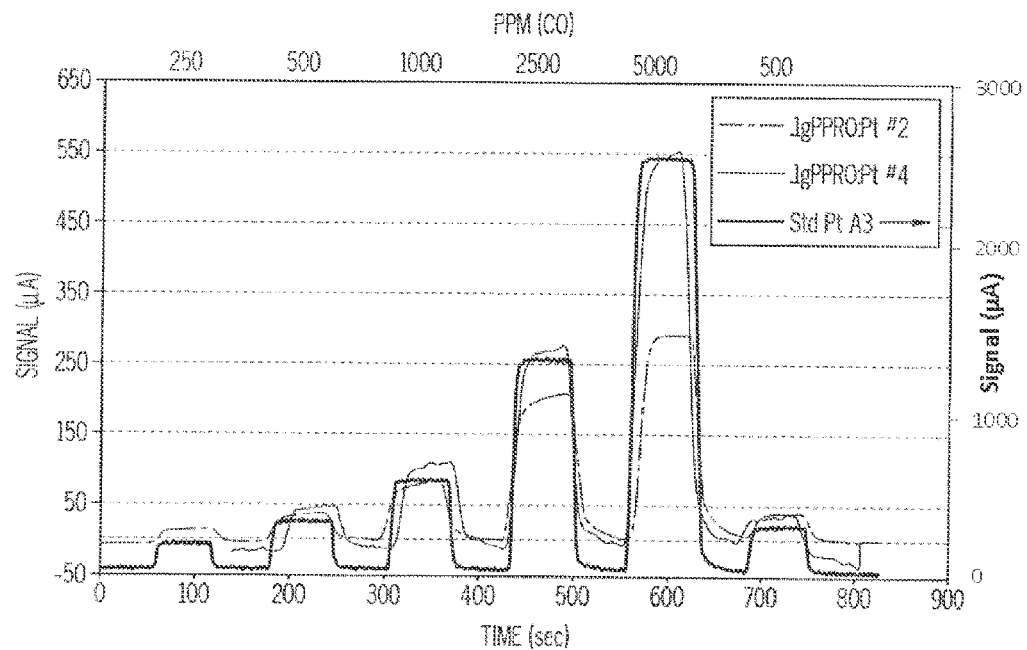
FIG. 15 graphically depicts the response signal in $\mu$Amps of electrodes formed with 5-7 $\mu$m PPRO powder particles.

FIG. 15 illustrates the response signal in μAmps of electrodes formed with 5-7 μm PPRO powder particles. The signal peaks are measuring, from left to right in FIG. 14, with the addition of 250 ppm CO, 500 ppm CO, 1000 ppm CO, 2500 ppm CO, 5000 ppm CO and 250 ppm CO, respectively. The PPRO powder electrode response was about 10-20% of the standard PTFE electrode response signal. PPRO electrodes responded and recovered slower than PTFE electrodes.

Experiment 3

In experiment 3, the catalyst ink suspension was prepared from polyethylene (PE) powder (a hydrophobic binder) instead of PTFE. PE binds at a lower temperature than PTFE. The PE powder particles used were about 2-4 μm. The optimized weight percentage of PE powder is lower than the optimized weight percentage of PTFE because PE has a lower density than PTFE. The density of PTFE is 2.0-2.2 g/cc and the density of PE is 0.97 g/cc. The optimized weight percentage of PTFE is 23-25 wgt % and the optimized weight percentage of PE is about 15-17 wgt %. The catalyst ink suspension formed with PE powder comprises a mixture of 1.44-1.45 g Pt (75-79 wgt %), 0.16±0.01 g graphite carbon (8-9 wgt %), 0.25-0.30 g PE powder (14-17 wgt %) combined with a 3 mL ethyl cellulose solution.

Figure 16:
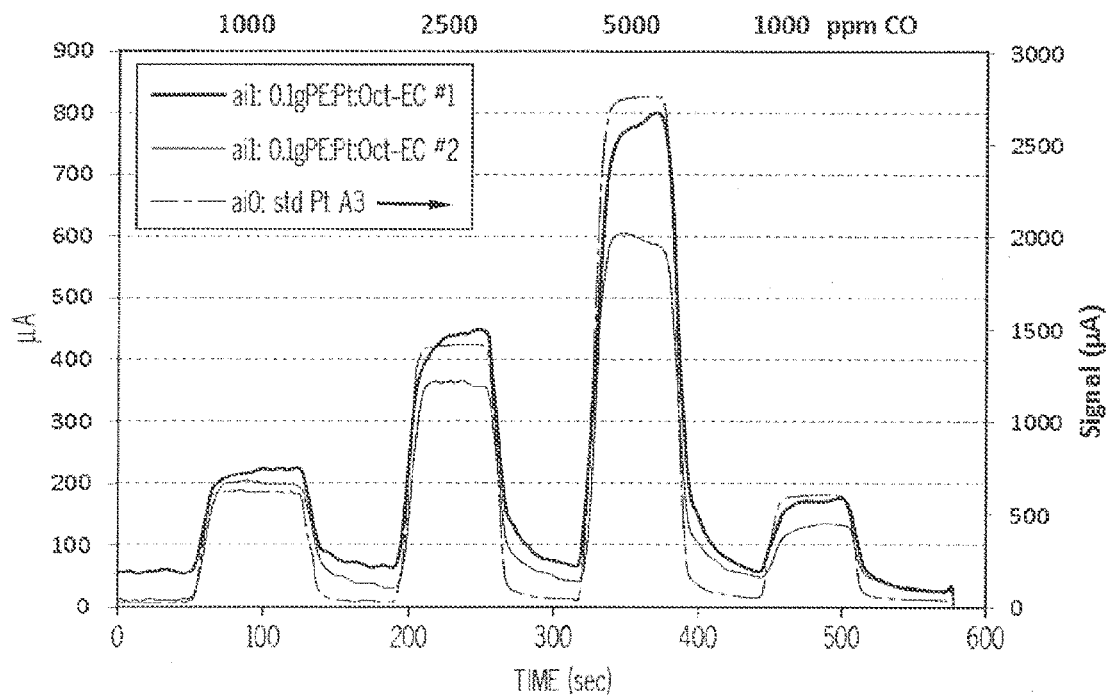
FIG. 16 graphically depicts the response signal in $\mu$Amps of electrodes formed with 2-4 $\mu$m PE powder particles.

FIG. 16 illustrates the response signal in μAmps of electrodes formed with 2-4 μm PE powder particles. The PE powder electrode response was about 25-30% of the standard PTFE electrode response. In this experiment, PE electrodes responded and recovered slower than PTFE electrodes. These results indicate a need to optimize the composition to improve the triple-phase boundary conditions.

Experiment 4

FIG. 17 illustrates the relationship between an electrode's CO sensitivity and the particle diameter of the polymers used in the electrode. It is possible to increase an electrode's CO sensitivity by reducing the particle diameter. The data in FIG. 17 illustrates the effect of polymer particle diameter on the sensitivity of electrodes comprising 17-23 wgt % polymer and 77-83 wgt % Pt. The CO sensitivity of the electrode varies with polymer particle diameter. According to this experiment, the sensitivity is independent of the specific polymer. If the requirements for a proper triple-phase boundary are met, polymer particle diameter becomes an important variable for adjusting CO sensitivity.

Experiment 5

FIG. 18 illustrates a relationship between gas port size and sensor to sensor consistency. In experiment 5, a sensor's gas port size was reduced from a 1.5 mm diameter to a 1.0 mm diameter. This reduction improved the sensor to sensor consistency to about ±5%.

Experiment 6

In experiment 6, the gas port area of a sensor was reduced from 3 $mm^2$ to 1 $mm^2$, a factor of 9. This reduced the sensor signal from 50 nA/ppm to 20 nA/ppm, a factor of about 2.5-3.0. Prior work by Dr. Stetter and colleagues has shown that sensor baseline currents decrease linearly with catalyst area and that signal to noise ratio improves as the perimeter to area ratio increases. For example, see Buttner, W. J., Maclay, G. J., and Stetter, J. R., "Chemical Sensing Apparatus and Methods," U.S. Pat. No. 5,512,882, issued Apr. 30, 1996; Buttner, W. J., Maclay, G. J., and Stetter, J. R., "Microfabricated Amperometric Gas Sensors with an Integrated Design," Sensors and Materials, 2, 99-106 (1990); Buttner, W. J., Maclay, G. J., and Stetter, J. R., "Microfabricated Amperometric Gas Sensors," IEEE Trans. On Electron Devices 35(6), 793 (1988); and Buttner, W. J., Maclay, G. J., and Stetter, J. R., "An Integrated Amperometric Microsensor," Sensors and Actuators, B1, 303-307, (1990).

It should be understood that, in general, the smaller sensor enabled by the design and methods of manufacture described herein result in sensors scalable to sizes not reached by previous technologies, operable over broad temperature ranges, and are low cost due to the scalable approach to production. The printed gas sensors described herein can also operate in environments having a wide range of relative humidities and have a scalable, optimized signal to noise ratio that can be used to detect low or high levels of a target gas.

The foregoing description of embodiments and examples of the invention has been presented for purposes of illustration and description. It is not intended to be exhaustive or to limit the invention to the forms described. Numerous modifications are possible in light of the above teachings. Some of those modifications have been discussed and others will be understood by those skilled in the art. While many of the embodiments herein disclose printed gas sensors that detect CO, the sensors and methods of manufacture described herein can be configured to measure other target gases such as $H_2S$, $NO_2$, $SO_2$, and the like. The embodiments were chosen and described in order to best illustrate the principles of the invention and various embodiments as are suited to the particular use contemplated. The scope of the invention is, of course, not limited to the examples or embodiments set forth herein, but can be employed in any number of applications and equivalent devices by those of ordinary skill in the art. Rather it is hereby intended the scope of the invention be defined by the claims appended hereto.

What is claimed is:

1. A printed gas sensor comprising:
   a first partially porous substrate comprising one or more gas access regions;
   one or more printed runners coupled to the first partially porous substrate, wherein the one or more printed runners are non-porous and electrically conductive;
   an encapsulation layer coupled to the first partially porous substrate and defining an electrolyte cavity positioned within the encapsulation layer;
   a non-ionically conductive wick positioned within the electrolyte cavity;
   one or more printed electrodes printed on the non-ionically conductive wick and in electrical communication with the one or more printed runners such that the one or more printed runners can transport an electronic signal produced by an electrochemical reaction at the one or more electrodes; and
   an electrolyte housed within the electrolyte cavity in communication with the electrodes capable of electrolytic communication among the electrodes.

2. The printed gas sensor of claim 1, wherein the first partially porous substrate comprises a porous PTFE in which one or more pores are partially blocked by a nonporous material adhered to the substrate.

3. The printed gas sensor of claim 2, wherein the one or more pores partially blocked by the nonporous material are patterned using a mask and lithographic agents.

4. The printed gas sensor of claim 1, further comprising a second partially porous substrate positioned between the first partially porous substrate and the encapsulation layer wherein the second partially porous substrate further comprises a slot and a porous PTFE disk is positioned within the slot.

5. The printed gas sensor of claim 1, further comprising a second partially porous substrate positioned between the first partially porous substrate and the encapsulation layer wherein the second partially porous substrate further comprises a slot and a porous polypropylene or polyethylene disk is positioned within the slot, wherein the electrolyte has an electrolyte contact angle that is greater than 70 degrees.

6. The printed gas sensor of claim 5, wherein the second partially porous substrate comprises polyethylene terephthalate.

7. The printed gas sensor of claim 1, wherein the encapsulation layer comprises an electrolyte fill port layer and an encapsulation cavity ring positioned between and coupled to both the first partially porous substrate and the electrolyte fill port layer thereby forming the electrolyte cavity within the encapsulation cavity ring.

8. The printed gas sensor of claim 1, wherein the non-ionically conductive wick comprises an electrolyte matrix selected from one or more of the following: compressible glass fiber, porous hydrophilic polypropylene or polyethylene, silica gel, or alumina.

9. The printed gas sensor of claim 1, wherein the one or more electrodes are printed on the non-ionically conductive wick before the non-ionically conductive wick is positioned within the electrolyte cavity.

10. The printed gas sensor of claim 9, wherein the one or more electrodes are printed on the non-ionically conductive wick using screen printing, gravure, inkjet printing, or stenciling.

11. The printed gas sensor of claim 1, wherein the one or more electrodes are partially embedded in the non-ionically conductive wick.

12. The printed gas sensor of claim 1, wherein the one or more gas access regions comprise holes.

13. The printed gas sensor of claim 1, wherein the first partially porous substrate is partially coated with polyimide such that one or more uncoated regions of the first partially porous substrate comprise the one or more gas access regions of the first partially porous substrate.

14. The printed gas sensor of claim 1, wherein a pressure sensitive adhesive is disposed between the first partially porous substrate and the encapsulation layer.

15. The printed gas sensor of claim 1, wherein a thermal adhesive is disposed between the first partially porous substrate and the encapsulation layer.

16. The printed gas sensor of claim 1, wherein the first partially porous substrate and the encapsulation layer are welded together using ultrasonic bonding.

17. The printed gas sensor of claim 1, wherein the one or more printed runners terminate at one or more contact points to provide electrical communication between the one or more electrodes and one or more electrical circuits.

18. The printed gas sensor of claim 1, wherein the one or more printed runners form vias for electrical connection to the electrodes and are impervious to gases and electrolytes.

19. The printed gas sensor of claim 1, wherein the electrolyte comprises a room temperature ionic liquid, ionic polymer, aqueous salt solution, base or acid solution or sulfuric acid.

20. The printed gas sensor of claim 1, wherein the electrolyte comprises a dry material transformable into a liquid electrolyte when exposed to a vapor.

21. The printed gas sensor of claim 1, wherein the electrolyte is in contact with the one or more electrodes thereby providing a location for an electrochemical reaction between the electrolyte, the one or more electrodes, and a target gas.

22. The printed gas sensor of claim 1, wherein the electrolyte is in contact with the one or more electrodes at a contact angle of greater than or equal to 70°.

23. The printed gas sensor of claim 1, wherein the electrolyte is in contact with the one or more electrodes at a contact angle of greater than or equal to 115°.

24. The printed gas sensor of claim 1, further comprising a filter assembly coupled to the first partially porous substrate, the filter assembly comprising:
   a fill port layer comprising one or more filter holes; and
   a filter cavity ring coupled to the fill port layer, the filter cavity ring comprising filter material positioned within the filter cavity ring and covering the one or more gas access regions of the first partially porous substrate.

25. The printed gas sensor of claim 1, further comprising a reservoir assembly coupled to the encapsulation layer, the reservoir assembly comprising:
   a reservoir fill port layer comprising one or more reservoir overflow holes;
   a reservoir cavity ring coupled to and positioned between the reservoir fill port layer and the encapsulation layer; and
   a reservoir plug coupled to the reservoir fill port layer opposite the reservoir cavity ring, wherein the reservoir plug hermetically seals the reservoir overflow holes of the reservoir fill port layer.

26. The printed gas sensor of claim 25, wherein a volume capacity of the reservoir assembly is about three to about six times greater than a volume capacity of the electrolyte in the encapsulation layer.

27. The printed gas sensor of claim 25, wherein a volume capacity of the reservoir assembly is about one to about 1.1 times greater than a volume capacity of the electrolyte in the encapsulation layer.

28. The printed gas sensor of claim 25, wherein the encapsulation layer further comprising a reservoir and wherein the volume capacity of the reservoir is about three to about six times greater than a volume capacity of the electrolyte in the encapsulation layer.

29. The printed gas sensor of claim 25, wherein the encapsulation layer further comprising a reservoir and wherein the volume capacity of the reservoir is about one to about 1.1 times greater than a volume capacity of the electrolyte in the encapsulation layer.

30. The printed gas sensor of claim 1, wherein the printed gas sensor is manufactured in a scalable manufacturing process configured to manufacture multiple printed gas sensors in one or more sheets of printed gas sensors.

31. The printed gas sensor of claim 1, wherein a size of the one or more gas access regions and a size of the one or more electrodes are directly correlated such that larger and/or more gas access regions correspond to larger and/or more electrodes.

32. The printed gas sensor of claim 31, wherein the size of the one or more electrodes is sized to minimize background noise.

33. The printed gas sensor of claim 31, wherein the size of the one or more electrodes is sized correlating to the maximum signal concentration of the printed gas sensor.

34. A printed gas sensor comprising:
- a solid substrate comprising one or more gas access regions;
- one or more printed runners positioned on the solid substrate;
- an encapsulation housing coupled to the solid substrate thereby forming an electrolyte cavity between the encapsulation housing and the solid substrate;
- a non-ionically conductive wick positioned within the electrolyte cavity;
- an electrolyte housed within the encapsulation housing; and
- one or more electrodes printed on the solid substrate within the electrolyte cavity, wherein the one or more electrodes are printed with catalyst inks and are in electrical communication with the one or more printed electrically conductive runners.

35. The printed gas sensor of claim 34, wherein the solid substrate comprises polycarbonate substrate, PET substrate, or a combination thereof.

36. The printed gas sensor of claim 34, wherein the encapsulation housing comprises polycarbonate substrate, PET substrate, or a combination thereof.

37. The printed gas sensor of claim 34, wherein the catalyst inks of the one or more electrodes are curable at temperatures lower than a deformation point of the solid substrate and a deformation point of the encapsulation housing.

38. The printed gas sensor of claim 34, wherein the catalyst inks are printed with a catalyst ink suspension comprising:
- a mixture comprising:
  - about 75-79% Pt;
  - about 8-9% graphite carbon; and
  - about 15-17% dry polypropylene powder; and
- a 3 mL ethyl cellulose solution.

39. The printed gas sensor of claim 38, wherein the ethyl cellulose solution further comprises octanol.

40. The printed gas sensor of claim 34, wherein the catalyst inks are printed on the solid substrate using process that involves sonication, dispersion, and stabilization.

41. The printed gas sensor of claim 34, wherein the one or more gas access regions comprise holes.

42. The printed gas sensor of claim 34, wherein the solid substrate is partially coated with polyimide such that one or more uncoated regions of the solid substrate comprise the one or more gas access regions of the solid substrate.

43. The printed gas sensor of claim 34, wherein a size of the one or more gas access regions and a size of the one or more electrodes are directly correlated such that larger and/or more gas access regions correspond to larger and/or more electrodes.

44. The printed gas sensor of claim 34, further comprising a filter assembly coupled to the solid substrate, the filter assembly comprising:
- a fill port layer comprising one or more filter holes; and
- a filter cavity ring coupled to the fill port layer, the filter cavity ring comprising filter material positioned within the filter cavity ring and covering the one or more gas access regions of the solid substrate.

45. The printed gas sensor of claim 34, further comprising a reservoir assembly coupled to the encapsulation housing, the reservoir assembly comprising:
- a reservoir fill port layer comprising one or more reservoir overflow holes;
- a reservoir cavity ring coupled to and positioned between the reservoir fill port layer and the encapsulation housing; and
- a reservoir plug coupled to the reservoir fill port layer opposite the reservoir cavity ring, wherein the reservoir plug hermetically seals the reservoir overflow holes of the reservoir fill port layer.

46. The printed gas sensor of claim 45, wherein a volume capacity of the reservoir assembly is about three to about six times greater than a volume capacity of the electrolyte.

47. The printed gas sensor of claim 34, wherein the printed gas sensor is manufactured in a scalable manufacturing process configured to manufacture the printed gas sensor in one or more sheets of printed gas sensors.

48. The printed gas sensor of claim 34, wherein the electrolyte comprises a dry material transformable into a liquid electrolyte when exposed to a vapor.

49. A printed gas sensor comprising:
- a high temperature upper substrate having one or more gas access regions;
- a high temperature lower substrate;
- one or more sealer spacers positioned between and coupled to the high temperature upper substrate and the high temperature lower substrate forming an electrolyte cavity there-between;
- an electrolyte housed within the electrolyte cavity;
- one or more electrodes positioned within the electrolyte cavity and printed on the high temperature upper and/or lower substrate;
- wherein the high temperature upper substrate and the high temperature lower substrate can withstand temperatures of at least 260° C.

50. The printed gas sensor of claim 49, wherein the high temperature upper substrate and the high temperature lower substrate comprise PTFE, polyimide, Kapton, polyethylene napthalate, polyvinyl pyrollidone combinations thereof.

51. The printed gas sensor of claim 49, further comprising a filter assembly coupled to the high temperature upper substrate, the filter assembly comprising:
- a fill port layer comprising one or more filter holes; and
- a filter cavity ring coupled to the fill port layer, the filter cavity ring comprising filter material positioned within the filter cavity ring and covering the one or more gas access regions of the high temperature upper substrate.

52. The printed gas sensor of claim 49, further comprising a reservoir assembly coupled to the high temperature lower substrate, the reservoir assembly comprising:
- a reservoir fill port layer comprising one or more reservoir overflow holes;
- a reservoir cavity ring coupled to and positioned between the reservoir fill port layer and the high temperature lower substrate; and
- a reservoir plug coupled to the reservoir fill port layer opposite the reservoir cavity ring, wherein the reservoir plug hermetically seals the reservoir overflow holes of the reservoir fill port layer.

53. The printed gas sensor of claim 52, wherein a volume capacity of the reservoir assembly is about three to about six times greater than a volume capacity of the electrolyte cavity.

54. The printed gas sensor of claim 49, wherein the printed gas sensor is manufactured in a scalable manufacturing process configured to manufacture the printed gas sensor in one or more sheets of printed gas sensors.

55. The printed gas sensor of claim 49, wherein the electrolyte comprises a dry material transformable into a liquid electrolyte when exposed to a vapor.

56. The printed gas sensor of claim 55, wherein a size of the one or more gas access regions and a size of the one or more electrodes are directly correlated such that larger and/or more gas access regions correspond to larger and/or more electrodes.

* * * * *